US006063949A

United States Patent [19]

Aulbach et al.

[11] Patent Number: 6,063,949

[45] **Date of Patent: *May 16, 2000**

[54] STEREORIGID METALLOCENE COMPOUND

[75] Inventors: Michael Aulbach, Hofheim; Frank Küber, Oberursel; Michael Riedel, Frankfurt; Freddy Helmer-Metzmann, Essenheim, all of Germany

[73] Assignee: Targor GmbH, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/665,923

[22] Filed: Jun. 19, 1996

[30] Foreign Application Priority Data

Jun. 19, 1995 [DE] Germany .......................... 195 22 105

[51] Int. Cl.[7] ...................................................... C07F 17/00

[52] U.S. Cl. .................................. 556/53; 556/9; 556/11; 556/12; 556/13; 556/19; 556/20; 556/42; 556/43; 556/51; 556/52; 556/57; 556/58; 502/152; 526/943; 526/160

[58] Field of Search .................................. 556/9, 11, 12, 556/13, 19, 20, 42, 43, 51, 52, 53, 57, 58

[56] References Cited

U.S. PATENT DOCUMENTS

| | | | |
|---|---|---|---|
| 4,892,851 | 1/1990 | Ewen et al. . | |
| 4,931,417 | 6/1990 | Miya et al. . | |
| 5,145,819 | 9/1992 | Winter et al. . | |
| 5,278,264 | 1/1994 | Spaleck et al. . | |
| 5,324,800 | 6/1994 | Welborn, Jr. et al. . | |
| 5,491,205 | 2/1996 | Langhauser et al. | 526/11 |
| 5,510,502 | 4/1996 | Sugano et al. | 556/11 |
| 5,565,534 | 10/1996 | Aulbach et al. | 526/160 |

FOREIGN PATENT DOCUMENTS

| | | |
|---|---|---|
| 0 129 368 | 12/1984 | European Pat. Off. . |
| 0 316 155 | 5/1989 | European Pat. Off. . |
| 0 351 392 | 1/1990 | European Pat. Off. . |
| 0 485 823 | 5/1992 | European Pat. Off. . |
| 0 530 647 | 3/1993 | European Pat. Off. . |
| 0 659 758 | 12/1994 | European Pat. Off. . |
| 0 661 300 | 12/1994 | European Pat. Off. . |
| 659758 | 6/1995 | European Pat. Off. . |

OTHER PUBLICATIONS

Gerhard Erker et al. *Kurtzmitteilung/Short Communication* "Synthesis of a Novel Annulated $C_1$–Bridged ansa–Metallocene System", Chem. Ber. 1994, 127, 1551–1553.

$1^{st}$ Journal of Organometallic Chemistry, Conference on Applied Organometallic Chemistry, p. 136 (1994).

Takaya Mise, et al, Excellent Stereoregular Isotactic Polymerizations of Propylene with $C_2$–Symmetric Silylene–Bridged Metallocene Catalysts, Chemistry Letters pp. 1852–1860 (1989).

*Primary Examiner*—David W. Wu
*Assistant Examiner*—Ling-Siu Choi
*Attorney, Agent, or Firm*—Connolly Bove Lodge & Hutz LLP

[57] ABSTRACT

The present invention relates to a stereorigid metallocene compound having as ligands at least two substituted or unsubstituted cyclopentadienyl groups which are connected to one another via a five-membered ring, where at least one cyclopentadienyl group is fused onto the five-membered ring and the ligand system of the stereorigid metallocene compound is different from 4-[$\eta^5$-3'-alkylcyclopentadienyl)-4,6,6-trimethyl-($\eta^5$-2-alkyl-4,5-tetrahydropentalene]. The metallocene compound of the invention is suitable as a catalyst component for olefin polymerization.

2 Claims, No Drawings

STEREORIGID METALLOCENE COMPOUND

The present invention relates to a special stereorigid metallocene compound and also a process for preparing polyolefins in the presence of this special stereorigid metallocene compound.

The preparation of polyolefins using soluble metallocene compounds in combination with aluminoxanes or other cocatalysts which, owing to their Lewis acidity, can convert the neutral metallocene into a cation and stabilize the latter is known from the literature (EP 129 368, EP 351 392).

The conference proceedings of the 1st Journal of Organometallic Chemistry Conference on Applied Organometallic Chemistry, page 136 describes metallocenes which have a substituted tricyclic hydrocarbon as ligand system.

The use of soluble metallocene compounds based on bis(cyclopentadienyl)zirconium dialkyl or dihalide in combination with oligomeric aluminoxanes gives atactic polymers which, owing to their unbalanced and inadequate product properties, are of little industrial importance. In addition, certain olefin copolymers are not obtainable.

Derivatives of zirconocene dichloride in which the two substituted cyclopentadienyl groups are connected to one another via a methylene, ethylene or dimethylsilylene bridge can, owing to their conformational rigidity, be used as catalysts for the isospecific polymerization of olefins (Chem. Lett. 1989, pp. 1853 to 1856 or EP-A 0 316 155). Metallocenes having (substituted) indenyl radicals as ligands are of particular importance for preparing highly isotactic polymers having high crystallinity and a high melting point (EP 485 823, EP 530 647).

Polyolefins whose property profile lies between these two extremes are also of great interest.

It is an object of the invention to provide a metallocene compound which avoids the disadvantages of the prior art and is suitable for preparing polyolefins.

The present invention accordingly provides a stereorigid metallocene compound having as ligands at least two substituted or unsubstituted cyclopentadienyl groups which are connected to one another via a five-membered ring, where at least one cyclopentadienyl group is fused onto the connecting five-membered ring and the ligand system of the stereorigid metallocene compound is different from 4-[$\eta^5$-3'-alkylcyclopentadienyl)-4,6,6-trimethyl-($\eta^5$-2-alkyl-4,5-tetrahydropentalene].

In determining the number of ring atoms in the connecting five-membered ring, those carbon atoms of the cyclopentadienyl group fused onto the connecting five-membered ring which are, owing to the fusion, part of the connecting five-membered ring are also counted. Possible substituents on the connecting five-membered ring are not counted here.

Preferably, there is a cyclopentadienyl group as substituent on the connecting five-membered ring (i.e. the cyclopentadienyl group is bonded via a covalent bond to the connecting five-membered ring), while a further cyclopentadienyl group is fused onto the connecting five-membered ring. The cyclopentadienyl groups can be unsubstituted or substituted. The cyclopentadienyl group fused onto the connecting five-membered ring is preferably unsubstituted.

Substituted cyclopentadienyl groups preferably bear one or more $C_1$–$C_{30}$-radicals such as $C_1$–$C_{10}$-alkyl, $C_6$–$C_{20}$-aryl (e.g. phenyl or naphthyl) or two or more of the $C_1$–$C_{30}$-radicals form a ring system.

Examples of substituted cyclopentadienyl groups are methylcyclopentadienyl, methyl-tert-butylcyclopentadienyl, tert-butylcycloepentadienyl, isopropylcyclopentadienyl, dimethylcyclopentadienyl, trimethylethylcyclopentadienyl, phenylcyclopentadienyl, diphenylcyclopentadienyl, indenyl, methylindenyl, ethylindenyl, tert-butylindenyl, trimethylsilylindenyl, methylphenylindenyl, ethylphenylindenyl, methylnaphthylindenyl, methylisopropylindenyl, benzoindenyl, methyl-4,5-benzoindenyl, methyl-α-acenaphthindenyl, methyldiisopropylindenyl, fluorenyl, methylfluorenyl or di-tert-butylfluorenyl.

The connecting five-membered ring is preferably aliphatic and can also contain heteroatoms such as nitrogen, oxygen, sulfur, silicon or germanium. The connecting five-membered ring can also bear substituents such as $C_1$–$C_{40}$-groups (e.g. $C_1$–$C_{10}$-alkyl or $C_6$–$C_{20}$-aryl).

The central unit $M^1R^x_n$ of the metallocene compound of the invention preferably consists of a transition metal atom $M^1$, particularly from group IIIb, IVb, Vb or VIb of the Periodic Table of the Elements, which bears n substituents $R^x$ which are identical or different and are preferably each a $C_1$–$C_{40}$-group, a halogen atom, an OH group or a hydrogen atom. The sum of the number of substituents $R^x$ and the number of the substituted or unsubstituted cyclopentadienyl groups (ligands) corresponds to the valence of the transition metal atom $M^1$.

The stereorigid metallocene compound of the invention preferably has the formula I (I)

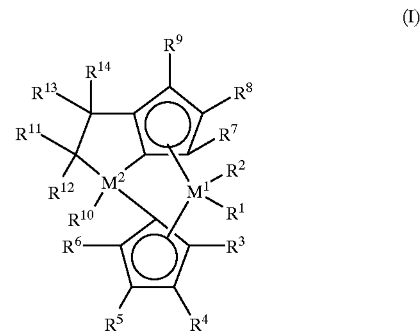

where $M^1$ is a metal of group IIIb, IVb, Vb or VIb of the Periodic Table, $M^2$ is carbon, silicon or germanium, $R^1$ and $R^2$ are identical or different and are each a hydrogen atom, a $C_1$–$C_{40}$-group such as a $C_1$–$C_{10}$-alkyl group, a $C_1$–$C_{10}$-alkoxy group, a $C_6$–$C_{10}$-aryl group, a $C_6$–$C_{25}$-aryloxy group, a $C_2$–$C_{10}$-alkenyl group, a $C_7$–$C_{40}$-arylalkyl group or a $C_7$–$C_{40}$-arylalkenyl group, an OH group, a halogen atom or $NR^{15}_2$, where $R^{15}$ is a halogen atom, a $C_1$–$C_{10}$-alkyl group or a $C_6$–$C_{10}$-aryl group, or $R^1$ and $R^2$ together with the atoms connecting them form a ring system, $R^3$, $R^4$, $R^5$, $R^6$, $R^7$, $R^8$ and $R^9$ are identical or different and are each a hydrogen atom, a halogen atom, a $C_1$–$C_{40}$-group such as a $C_1$–$C_{10}$-alkyl group which can be halogenated, a $C_6$–$C_{30}$-aryl group which can be halogenated, a $C_6$–$C_{20}$-aryloxy group, a $C_2$–$C_{12}$-alkenyl group, a $C_7$–$C_{40}$-arylalkyl group, a $C_7$–$C_{40}$-alkylaryl group or a $C_8$–$C_{40}$-arylalkenyl group, an —$SiR^{15}_3$, —$NR^{15}_2$—, —$SiOR^{15}_3$—, —$SiSR^{15}_3$— or —$PR^{15}_2$ radical, where $R^{15}$ are identical or different and are each a halogen atom, a $C_1$–$C_{10}$-alkyl group or a $C_6$–$C_{10}$-aryl group or form a ring system, or two or more adjacent radicals $R^3$, $R^4$, $R^5$, $R^6$, $R^7$, $R^8$ and $R^9$ together with the atoms connecting them form a ring system which preferably contains from 4 to 40, particularly preferably from 6 to 20, carbon atoms, $R^{10}$ is a hydrogen atom or a $C_1$–$C_{40}$-group such as a $C_1$–$C_{20}$-alkyl group, a $C_1$–$C_{10}$-alkoxy group, a $C_6$–$C_{20}$-aryl group, a $C_6$–$C_{20}$-aryloxy group, a $C_2$–$C_{12}$-alkenyl group, a $C_7$–$C_{40}$-arylalkyl group, a $C_7$–$C_{40}$-alkylaryl group or a $C_8$–$C_{40}$-arylalkenyl group, which can each bear radicals —$NR^{15}_3$, —$SiR^{15}_3$, —$SR^{15}_2$ or —$OSiR^{15}_3$, where $R^{15}$ is a halogen atom, a $C_1$–$C_{10}$-alkyl group or a $C_6$–$C_{10}$-aryl group, or $R^{10}$ is connected to one or more of the radicals $R^3$, $R^4$, $R^5$ and $R^6$, $R^{11}$ and $R^{12}$ are identical or different and are each a hydrogen atom, a $C_1$–$C_{40}$-group such as a $C_1$–$C_{20}$-alkyl group, a $C_1$–$C_{10}$-alkoxy group, a $C_6$–$C_{20}$-aryl group, a $C_2$–$C_{12}$-alkenyl group, a $C_7$–$C_{40}$-arylalkyl group, a $C_7$–$C_{40}$-alkylaryl group or a $C_8$–$C_{40}$-arylalkenyl group, which can each bear radicals such as a halogen atom, —$NR^{15}_3$, —$SR^{15}_2$, —$SiR^{15}_3$ or —$OSiR^{15}_3$ where $R^{15}$ is a halogen atom, a $C_1$–$C_{10}$-alkyl group or a $C_6$–$C_{10}$-aryl group, $R^{13}$ and $R^{14}$ are identical or different and are each a hydrogen atom, a $C_1$–$C_{40}$-group such as a $C_1$–$C_{20}$-alkyl group, a $C_1$–$C_{10}$-alkoxy group, a $C_6$–$C_{20}$-aryl group, a $C_2$–$C_{12}$-alkenyl group, a $C_7$–$C_{40}$-arylalkyl group, a $C_7$–$C_{40}$-alkylaryl group or a $C_8$–$C_{40}$-arylalkenyl group, which can each bear radicals such as a halogen atom, —$NR^{15}_3$, —$SR^{15}_2$, —$SiR^{15}_3$ or —$OSiR^{15}_3$, where $R^{15}$ is a halogen atom, a $C_1$–$C_{10}$-alkyl group or a $C_6$–$C_{10}$-aryl group, where in the case of M being carbon and $R^{10}$, $R^{13}$ and $R^{14}$ being methyl, at least one of the radicals $R^3$, $R^5$, $R^6$, $R^7$ and $R^9$ is different from hydrogen and/or $R^8$ is hydrogen.

For compounds of the formula I, it is preferred that $M^1$ is a metal of group IVb of the Periodic Table of the Elements such as titanium, zirconium or hafnium, in particular zirconium, $R^1$ and $R^2$ are identical and are each a $C_1$–$C_4$-alkyl group or a halogen atom such as fluorine, chlorine, bromine or iodine, in particular chlorine, $R^3$, $R^4$, $R^5$, $R^6$, $R^7$, $R^8$ and $R^9$ are identical or different and are each a hydrogen atom, a $C_1$–$C_{10}$-alkyl group or a $C_6$–$C_{24}$-aryl group, or two or more adjacent radicals $R^3$, $R^4$, $R^5$, $R^6$, $R^7$, $R^8$ and $R^9$ together with the atoms connecting them form an aromatic or aliphatic ring system having from 4 to 20 carbon atoms, $R^{10}$ is a hydrogen atom, a $C_6$–$C_{24}$-aryl group or a $C_1$–$C_{10}$-alkyl group, in particular a $C_1$–$C_4$-alkyl group, $M^2$ is carbon, $R^{11}$ and $R^{12}$ are identical or different and $R^{11}$ is a hydrogen atom, a $C_1$–$C_{10}$-group, in particular a $C_1$–$C_4$-alkyl group or a $C_6$–$C_{10}$-aryl group and $R^{12}$ is a hydrogen atom and $R^{13}$ and $R^{14}$ are identical or different and are each a hydrogen atom, a $C_1$–$C_{10}$-group, in particular a $C_1$–$C_4$-alkyl group or a $C_6$–$C_{10}$-aryl group, and at least one of the radicals $R^3$, $R^5$, $R^6$, $R^7$ and $R^9$ is different from hydrogen and/or $R^8$ is hydrogen.

Particular preference is given to compounds of the formula I in which $M^1$ is zirconium, $R^1$ and $R^2$ are identical and are each a halogen atom, in particular chlorine, $R^3$, $R^4$, $R^5$, $R^6$, $R^7$ and $R^9$ are identical or different and are each a hydrogen atom or a $C_1$–$C_4$-alkyl group such as methyl, ethyl, propyl, isopropyl, butyl or isobutyl or a $C_6$–$C_{14}$-aryl group such as phenyl or naphthyl, or $R^3$ and $R^4$ and/or $R^5$ and $R^6$ together with the atoms connecting them form an aromatic hydrocarbon ring system having from 4 to 20 carbon atoms, in particular a six-membered ring which in turn can be substituted, $R^8$ is a hydrogen atom, $M^2$ is a carbon atom, $R^{10}$ is a hydrogen atom, a $C_1$–$C_6$-alkyl group, in particular methyl, or a $C_6$–$C_{10}$-aryl group, in particular phenyl, $R^{11}$ and $R^{12}$ are identical and are each a hydrogen atom and $R^{13}$ and $R^{14}$ are identical or different and are each a methyl or a phenyl group.

Examples of metallocene compounds of the invention are:

[4-($\eta^5$-cyclopentadienyl)($\eta^5$-4,5-tetrahydropentalene)] dichlorotitanium, [4-($\eta^5$-cyclopentadienyl)($\eta^5$-4,5-tetrahydropentalene)]dichlorozirconium, [4-($\eta^5$-cyclopentadienyl)($\eta^5$-4,5-tetrahydropentalene)] dichlorohafnium,

[4-($\eta^5$-cyclopentadienyl)-4-methyl-($\eta^5$-4,5-tetrahydropentalene)]dichlorozirconium, [4-($\eta^5$-cyclopentadienyl)-4-ethyl-($\eta^5$-4,5-tetrahydropentalene)] dichlorozirconium, [4-($\eta^5$-cyclopentadienyl)-4-phenyl-($\eta^5$-4,5-tetrahydropentalene)]dichlorozirconium,

[4-($\eta^5$-cyclopentadienyl)-6-methyl-6-phenyl-($\eta^5$-4,5-tetrahydropentalene)]-dichlorozirconium, [4-($\eta^5$-cyclopentadienyl)-4,6-dimethyl-6-phenyl-($\eta^5$-4,5-tetrahydropentalene)]dichlorozirconium, [4-($\eta^5$-cyclopentadienyl)-4-ethyl-6-methyl-6-phenyl-($\eta^5$-4,5-tetrahydropentalene)]dichlorozirconium, [4-($\eta^5$-cyclopentadienyl)-4-phenyl-6-methyl-6-phenyl-($\eta^5$-4,5-tetrahydropentalene)]dichlorozirconium,

[4-($\eta^5$-cyclopentadienyl)-6,6-diphenyl-($\eta^5$-4,5-tetrahydropentalene)]-dichlorozirconium, [4-($\eta^5$-cyclopentadienyl)-4-methyl-6,6-diphenyl-($\eta^5$-4,5-tetrahydropentalene)]dichlorozirconium, [4-($\eta^5$-cyclopentadienyl)-4,6,6-triphenyl-($\eta^5$-4,5-tetrahydropentalene)]-dichlorozirconium,

[4-($\eta^5$-cyclopentadienyl)-6,6-dimethyl-($\eta^5$-4,5-tetrahydropentalene)]-dichlorozirconium, [4-($\eta^5$-cyclopentadienyl)-4-phenyl-6,6-dimethyl-($\eta^5$-4,5-tetrahydropentalene)]dichlorozirconium,

[4-($\eta^5$-cyclopentadienyl)-6-methyl-($\eta^5$-4,5-tetrahydropentalene)]dichlorozirconium, [4-($\eta^5$-cyclopentadienyl)-6-butyl-($\eta^5$-4,5-tetrahydropentalene)] dichlorozirconium, [4-($\eta^5$-cyclopentadienyl)-6-phenyl-($\eta^5$-4,5-tetrahydropentalene)]dichlorozirconium,

[4-($\eta^5$-cyclopentadienyl)-4,6-dimethyl-($\eta^5$-4,5-tetrahydropentalene)]dichlorozirconium, [4-($\eta^5$-cyclopentadienyl)-4-phenyl-6-methyl-($\eta^5$-4,5-tetrahydropentalene)]-dichlorozirconium,

[4-($\eta^5$-cyclopentadienyl)-4-methyl-6-phenyl-($\eta^5$-4,5-tetrahydropentalene)]-dichlorozirconium) [4-($\eta^5$-cyclopentadienyl)-4-phenyl-6-phenyl-($\eta^5$-4,5-tetrahydropentalene)]-dichlorozirconium,

[4-($\eta^5$-indenyl)($\eta^5$-4,5-tetrahydropentalene)] dichlorotitanium, [4-($\eta^5$-indenyl)($\eta^5$-4,5-tetrahydropentalene)]dichlorozirconium, [4-($\eta^5$-indenyl) ($\eta^5$-4,5-tetrahydropentalene)]dichlorohafnium,

[4-($\eta^5$-indenyl)-4-methyl-($\eta^5$-4,5-tetrahydropentalene)] dichlorozirconium, [4-($\eta^5$-indenyl)-4-phenyl-($\eta^5$-4,5-tetrahydropentalene)]dichlorozirconium,

[4-($\eta^5$-indenyl)-6-methyl-6-phenyl-($\eta^5$-4,5-tetrahydropentalene)]dichlorozirconium, [4-($\eta^5$-indenyl)-4,6-dimethyl-6-phenyl-($\eta^5$-4,5-tetrahydropentalene)] dichlorozirconium, [4-($\eta^5$-indenyl)-4-phenyl-6-methyl-6-phenyl-($\eta^5$-4,5-tetrahydropentalene)]-dichlorozirconium,

[4-($\eta^5$-indenyl)-6,6-diphenyl-($\eta^5$-4,5-tetrahydropentalene)] dichlorozirconium, [4-($\eta^5$-indenyl)-4-methyl-6,6-diphenyl-($\eta^5$-4,5-tetrahydropentalene)]-dichlorozirconium, [4-($\eta^5$-indenyl)-4,6,6-triphenyl-($\eta^5$-4,5-tetrahydropentalene)]-dichlorozirconium,

[4-($\eta^5$-indenyl)-6,6-dimethyl-($\eta^5$-4,5-tetrahydropentalene)] dichlorozirconium, [4-($\eta^5$-indenyl)-4-ethyl-6,6-dimethyl-($\eta$-4,5-tetrahydropentalene)]-dichlorozirconium, [4-($\eta^5$-indenyl)-4-phenyl-6,6-dimethyl-($\eta^5$-4,5-tetrahydropentalene)]-dichlorozirconium,

[4-($\eta^5$-indenyl)-6-methyl-($\eta^5$-4,5-tetrahydropentalene)] dichlorozirconium, [4-($\eta^5$-indenyl)-6-ethyl-($\eta^5$-4,5-tetrahydropentalene)]dichlorozirconium, [4-($\eta^5$-indenyl)-6-phenyl-($\eta^5$-4,5-tetrahydropentalene)] dichlorozirconium,

[4-($\eta^5$-indenyl)-4,6-dimethyl-($\eta^5$-4,5-tetrahydropentalene)] dichlorozirconium, [4-($\eta^5$-indenyl)-4-phenyl-6-methyl-($\eta^5$-4,5-tetrahydropentalene)]dichlorozirconium,

[4-($\eta^5$-indenyl)-4-methyl-6-phenyl-($\eta^5$-4,5-tetrahydropentalene)]dichlorozirconium, [4-($\eta^5$-indenyl)-4-phenyl-6-phenyl-($\eta^5$-4,5-tetrahydropentalene)] dichlorozirconium, [4-($\eta^5$-fluorenyl)($\eta^5$-4,5-tetrahydropentalene)]dichlorotitanium, [4-($\eta^5$-fluorenyl) ($\eta^5$-4,5-tetrahydropentalene)]dichlorozirconium, [4-($\eta^5$-fluorenyl)($\eta^5$-4,5-tetrahydropentalene)]dichlorohafnium,

[4-($\eta^5$-fluorenyl)-4-methyl-($\eta^5$-4,5-tetrahydropentalene)] dichlorozirconium, [4-($\eta^5$-fluorenyl)-4-phenyl-($\eta^5$-4,5-tetrahydropentalene)]dichlorozirconium,

[4-($\eta^5$-fluorenyl)-6-methyl-6-phenyl-($\eta^5$-4,5-tetrahydropentalene)]dichlorozirconium, [4-($\eta^5$-fluorenyl)-4,6-dimethyl-6-phenyl-($\eta^5$-4,5-tetrahydropentalene)]-dichlorozirconium, [4-($\eta^5$-fluorenyl)-4-phenyl-6-methyl-6-phenyl-($\eta^5$-4,5-tetrahydropentalene)]dichlorozirconium,

[4-($\eta^5$-fluorenyl)-6,6-diphenyl-($\eta^5$-4,5-tetrahydropentalene)]dichlorozirconium, [4-($\eta^5$-fluorenyl)-4-methyl-6,6-diphenyl-($\eta^5$-4,5-tetrahydropentalene)]dichlorozirconium, [4-($\eta^5$-fluorenyl)-4,6,6-triphenyl-($\eta^5$-4,5-tetrahydropentalene)] dichlorozirconium,

[4-($\eta^5$-fluorenyl)-6,6-dimethyl-($\eta^5$-4,5-tetrahydropentalene)]dichlorozirconium, [4-($\eta^5$-fluorenyl)-4-phenyl-6,6-dimethyl-($\eta^5$-4,5-tetrahydropentalene)]-dichlorozirconium,

[4-($\eta^5$-fluorenyl)-6-methyl-($\eta^5$-4,5-tetrahydropentalene)] dichlorozirconium, [4-($\eta^5$-fluorenyl)-6-phenyl-($\eta^5$-4,5-tetrahydropentalene)]dichlorozirconium,

[4-($\eta^5$-fluorenyl)-4,6-dimethyl-($\eta^5$-4,5-tetrahydropentalene)]dichlorozirconium, [4-($\eta^5$-fluorenyl)-4-phenyl-6-methyl-($\eta^5$-4,5-tetrahydropentalene)]dichlorozirconium, [4-($\eta^5$-fluorenyl)-4-methyl-6-phenyl-($\eta^5$-4,5-tetrahydropentalene)]dichlorozirconium, [4-($\eta^5$-fluorenyl)-4-phenyl-6-phenyl-($\eta^5$-4,5-tetrahydropentalene)]dichlorozirconium, [4-($\eta^5$-3,5,6,7-tetrahydroindenyl)($\eta^5$-4,5-tetrahydropentalene)] dichlorotitanium, [4-($\eta^5$-4,5,6,7-tetrahydroindenyl)($\eta^5$-4,5-tetrahydropentalene)]dichlorozirconium, [4-($\eta^5$-4,5,6,7-tetrahydroindenyl)($\eta^5$-4,5-tetrahydropentalene)] dichlorohafnium,

[4-($\eta^5$-4,5,6,7-tetrahydroindenyl)-4-methyl-($\eta^5$-4,5-tetrahydropentalene)]-dichlorozirconium, [4-($\eta^5$-4,5,6,7-tetrahydroindenyl)-4-phenyl-($\eta^5$-4,5-tetrahydropentalene)]-dichlorozirconium,

[4-($\eta^5$-4,5,6,7-tetrahydroindenyl)-6-methyl-6-phenyl-($\eta^5$-4,5-tetrahydropentalene)]dichlorozirconium, [4-($\eta^5$-4,5,6,7-tetrahydroindenyl)-4,6-dimethyl-6-phenyl-($\eta^5$-4,5-tetrahydropentalene)]dichlorozirconium, [4-($\eta^5$-4,5,6,7-tetrahydroindenyl)-4-phenyl-6-methyl-6-phenyl-($\eta^5$-4,5-tetrahydropentalene)]dichlorozirconium,

[4-($\eta^5$-4,5,6,7-tetrahydroindenyl)-6,6-diphenyl-($\eta^5$-4,5-tetrahydropentalene)]dichlorozirconium, [4-($\eta^5$-4,5,6,7-tetrahydroindenyl)-4-methyl-6,6-diphenyl-($\eta^5$-4,5-tetrahydropentalene)]dichlorozirconium, [4-($\eta^5$-4,5,6,7-tetrahydroindenyl)-4,6,6-triphenyl-($\eta^5$-4,5-tetrahydropentalene)]dichlorozirconium,

[4-($\eta^5$-4,5,6,7-tetrahydroindenyl)-6,6-dimethyl-($\eta^5$-4,5-tetrahydropentalene)]dichlorozirconium, [4-($\eta^5$-4,5,6,7-tetrahydroindenyl)-4-ethyl-6,6-dimethyl-($\eta^5$-4,5-tetrahydropentalene)]dichlorozirconium, [4-($\eta^5$-4,5,6,7-tetrahydroindenyl)-4-phenyl-6,6-dimethyl-($\eta^5$-4,5-tetrahydropentalene)]dichlorozirconium,

[4-($\eta^5$-4,5,6,7-tetrahydroindenyl)-6-methyl-($\eta^5$-4,5-tetrahydropentalene)]-dichlorozirconium, [4-($\eta^5$-4,5,6,7-tetrahydroindenyl)-6-phenyl-($\eta^5$-4,5-tetrahydropentalene)]-dichlorozirconium,

[4-($\eta^5$-4,5,6,7-tetrahydroindenyl)-4,6-dimethyl-($\eta^5$-4,5-tetrahydropentalene)]dichlorozirconium, [4-($\eta^5$-4,5,6,7-tetrahydroindenyl)-4-phenyl-6-methyl-($\eta^5$-4,5-tetrahydropentalene)]dichlorozirconium,

[4($\eta^5$-4,5,6,7-tetrahydroindenyl)-4-methyl-6-phenyl-($\eta^5$-4,5-tetrahydropentalene)]dichlorozirconium, [4-($\eta^5$-4,5,6,7-tetrahydroindenyl)-4-phenyl-6-phenyl-($\eta^5$-4,5-tetrahydropentalene)]dichlorozirconium,

[4-($\eta^5$-3'-methylcyclopentadienyl)-($\eta^5$-4,5-tetrahydropentalene)]dichlorozirconium, [4-($\eta^5$-3'-isopropylcyclopentadienyl)-($\eta^5$-4,5-tetrahydropentalene)]dichlorozirconium, [4-($\eta^5$-3'-benzylcyclopentadienyl)-($\eta^5$-4,5-tetrahydropentalene)] dichlorozirconium,

[4-($\eta^5$-3'-methylcyclopentadienyl)-4-methyl-($\eta^5$-4,5-tetrahydropentalene)]-dichlorozirconium, [4-($\eta^5$-3'-isopropylcyclopentadienyl)-4-methyl-($\eta^5$-4,5-tetrahydropentalene)]dichlorozirconium, [4-($\eta^5$-3'-benzylcyclopentadienyl)-4-methyl-($\eta^5$-4,5-tetrahydropentalene)]-dichlorozirconium,

[4-($\eta^5$-3'-methylcyclopentadienyl)-4-phenyl-($\eta^5$-4,5-tetrahydropentalene)]-dichlorozirconium, [4-($\eta^5$-3'-isopropylcyclopentadienyl)-4-phenyl-($\eta^5$-4,5-tetrahydropentalene)]dichlorozirconium, [4-($\eta^5$-3'-benzylcyclopentadienyl)-4-phenyl-($\eta^5$-4,5-tetrahydropentalene)]-dichlorozirconium,

[4-($\eta^5$-3'-methylcyclopentadienyl)-4,6-dimethyl-($\eta^5$-4,5-tetrahydropentalene)]dichlorozirconium, [4-($\eta^5$-3'-isopropylcyclopentadienyl)-4,6-dimethyl-($\eta^5$-4,5-tetrahydropentalene)]dichlorozirconium, [4-($\eta^5$-3'-benzylcyclopentadienyl)-4,6-dimethyl-($\eta^5$-4,5-tetrahydropentalene)]dichlorozirconium,

[4-($\eta^5$-3'-methylcyclopentadienyl)-4-methyl-6-phenyl-($\eta^5$-4,5-tetrahydropentalene)]dichlorozirconium, [4-($\eta^5$-3'-isopropylcyclopentadienyl)-4-methyl-6-phenyl-($\eta^5$-4,5-tetrahydropentalene)]dichlorozirconium, [4-($\eta^5$-3'-benzylcyclopentadienyl)-4-methyl-6-phenyl-($\eta^5$-4,5-tetrahydropentalene)]dichlorozirconium,

[4-($\eta^5$-3'-methylcyclopentadienyl)-4,6-dimethyl-6-phenyl-($\eta^5$-4,5-tetrahydropentalene)]dichlorozirconium, [4-($\eta^5$-3'-isopropylcyclopentadienyl)-4,6-dimethyl-6-phenyl-($\eta^5$-4,5-tetrahydropentalene)]dichlorozirconium, [4-($\eta^5$-3'-benzylcyclopentadienyl)-4,6-dimethyl-6-phenyl-($\eta^5$-4,5-tetrahydropentalene)]dichlorozirconium,

[4-($\eta^5$-3'-methylcyclopentadienyl)-2-methyl-($\eta^5$-4,5-tetrahydropentalene)]-dichlorozirconium, [4-($\eta^5$-3'-isopropylcyclopentadienyl)-2-isopropyl-($\eta^5$-4,5-tetrahydropentalene)]dichlorozirconium, [4-($\eta^5$-3'-benzylcyclopentadienyl)-2-benzyl-($\eta^5$-4,5-tetrahydropentalene)]-dichlorozirconium, [4-($\eta^5$-3'-isopropylcyclopentadienyl)-2-benzyl-($\eta^5$-4,5-tetrahydropentalene)]dichlorozirconium, [4-($\eta^5$-3'-benzylcyclopentadienyl)-2-isopropyl-($\eta^5$-4,5-tetrahydropentalene)]dichlorozirconium,

[4-($\eta^5$-3'-methylcyclopentadienyl)-2,4-dimethyl-($\eta^5$-4,5-tetrahydropentalene)]dichlorozirconium, [4-($\eta^5$-3'-isopropylcyclopentadienyl)-2-isopropyl-4-methyl-($\eta^5$-4,5-tetrahydropentalene)]dichlorozirconium, [4-($\eta^5$-3'-benzylcyclopentadienyl)-2-benzyl-4-methyl-($\eta^5$-4,5-tetrahydropentalene)]dichlorozirconium,

[4-($\eta^5$-3'-isopropylcyclopentadienyl)-2-benzyl-4-methyl-($\eta^5$-4,5-tetrahydropentalene)]dichlorozirconium, [4-($\eta^5$-3'-benzylcyclopentadienyl)-2-isopropyl-4-methyl-($\eta^5$-4,5-tetrahydropentalene)]dichlorozirconium.

The naming of the abovementioned compounds of the invention will be illustrated with the aid of the compound [4-($\eta^5$-3'-isopropylcyclopentadienyl)-6-phenyl-($\eta^5$-4,5-tetrahydropentalene)]dichlorozirconium.

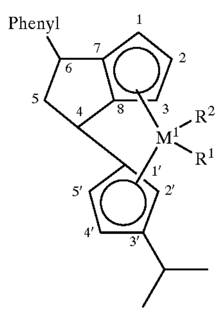

The preparation of the metallocenes of the invention will be illustrated by the following reaction scheme for metallocenes of the formula VI. In this scheme, $M^4$ is a metal of main group Ia, IIa or IIIa of the Periodic Table of the Elements, Hal is a halogen atom, the radicals $R^3$–$R^{11}$, $R^{13}$ and $R^{14}$ are as defined for formula I and $R^{12}$ is hydrogen.

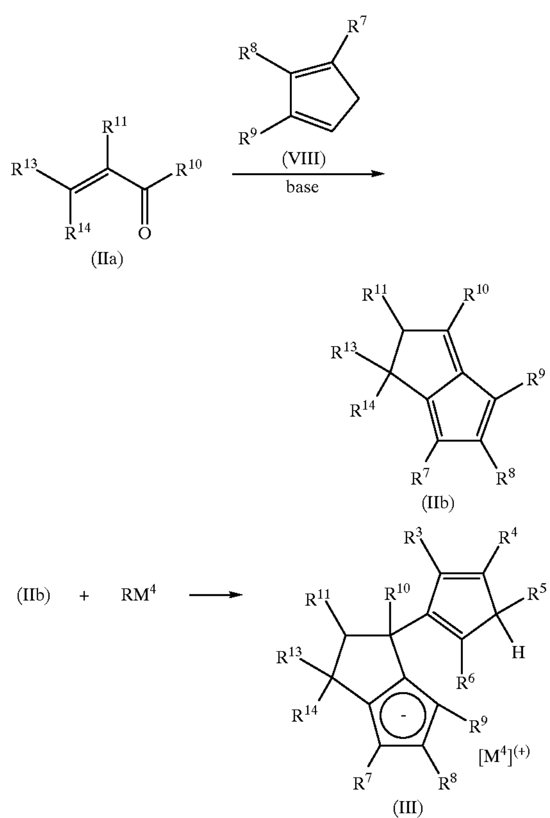

-continued

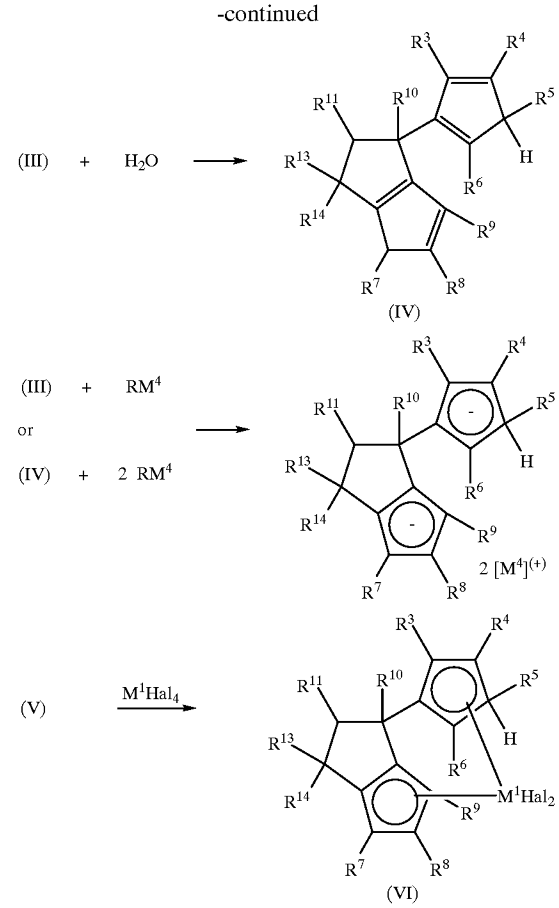

The compounds of the formula lib can be prepared from α,β-unsaturated ketones (Chem. Ber. 123, 549 (1990), J. Org. Chem. 54, 4981 (1989)) by literature methods.

The reaction of the compound of the formula lib to give the ligand system III is carried out by reaction with a compound $RM^4$ which can be an organometallic compound (e.g. cyclopentadienyllithium, indenyllithium, fluorenyllithium) or a Grignard reagent (e.g. cyclopentadienylMgHal, indenylMgHal, fluorenylMgHal).

The salts of the formula III can be converted directly into the corresponding dianion compounds of the formula V by deprotonation with, for example, butyllithium. The hydrolysis of compound III leads to formation of the biscyclopentadiene compound IV which is formed as a mixture of structural isomers and can be purified by chromatography.

Double deprotonation of IV with, for example, butyllithium forms the dianion compound of the formula V which is reacted with $M^1Hal_4$ to give the metallocene of the formula VI.

Metallocenes of the formula VI can be reacted with organometallic compounds such as Grignard reagents or hydrocarbon-lithium reagents to give metallocenes of the formula I in which $R^1$ and $R^2$ are not halogen. The reaction to give the bridged metallocenes of the formula VI and the isolation of the desired complexes is known in principle. For this purpose, the dianion of the formula V is reacted in an inert solvent with the corresponding metal halide such as zirconium tetrachloride. The metallocenes of the formula VI can also be synthesized directly from the difulvenes of the formula II without isolation of the intermediates.

Suitable solvents are aliphatic or aromatic solvents such as hexane or toluene, ether solvents such as tetrahydrofuran or diethyl ether or halogenated hydrocarbons such as methylene chloride or halogenated aromatic hydrocarbons such as o-dichlorobenzene.

A further possible way of preparing the metallocene compounds of the invention is the reaction of the ligand precursor VII with the cyclopentadiene VIII which can each be prepared by procedures known from the literature. According to one procedure known from the literature, the compounds IX can be thermally cyclized to give the ligand precursors X (Chem. Ber. 120, 1611 (1987)). The reaction of X to XI is carried out using an organometallic compound (for example cyclopentadienyllithium, indenyllithium, fluorenyllithium) or Grignard reagents.

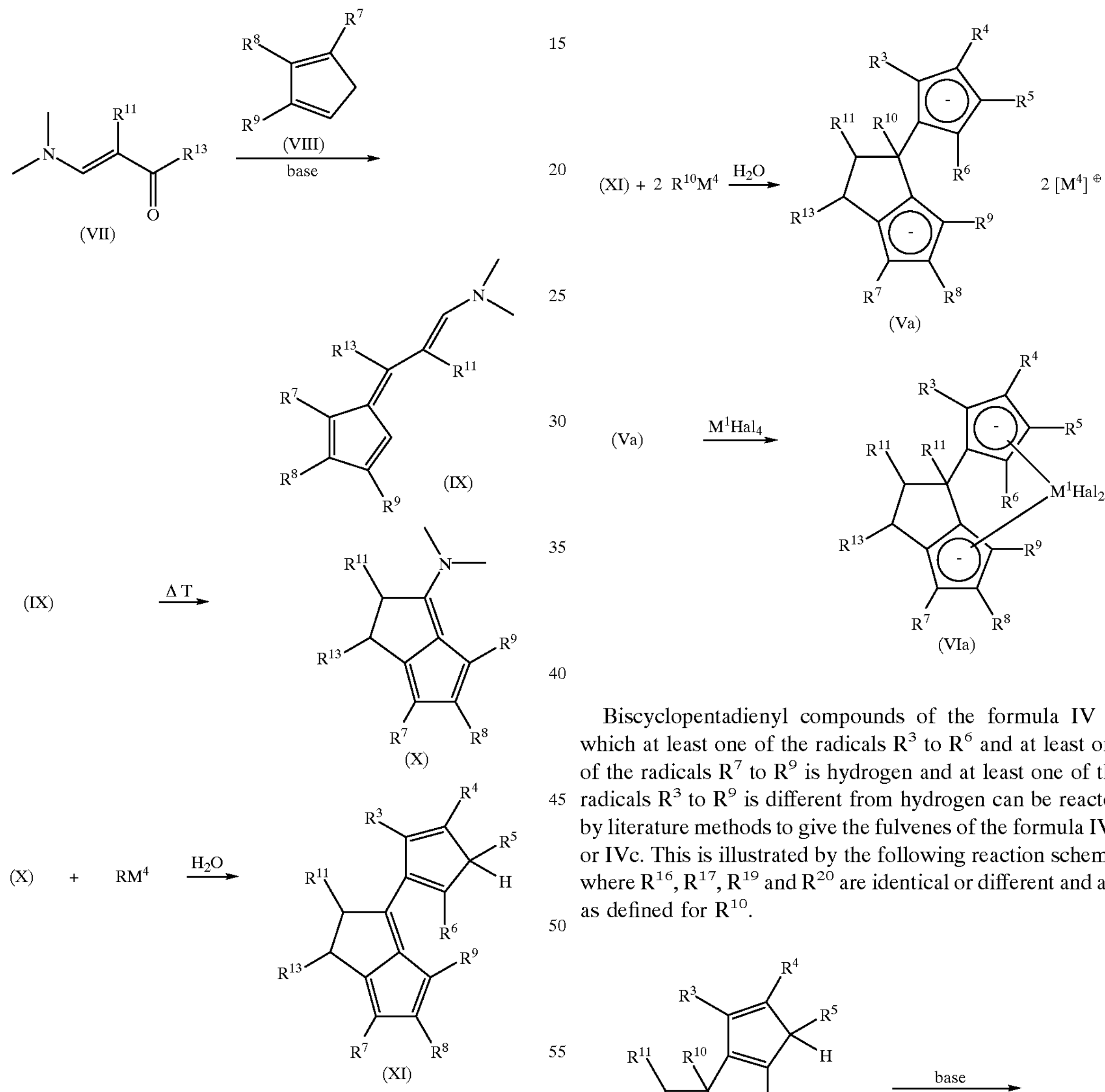

The dianion compound of the formula Va can be obtained directly by reaction of X with an organometallic reagent (for example phenyllithium, methyllithium, n-butyllithium or Grignard reagents). The hydrolysis of Va with water leads to generation of the ligand precursors IV.

The reaction to form the bridged metallocenes of the formula VIa and the isolation of the desired complexes is known in principle. For this purpose, the dianion of the formula Va is reacted in an inert solvent with the corresponding metal halide such as zirconium tetrachloride. The metallocenes of the formula VIa can also be synthesized directly from the fulvenes of the structure X without isolation of the intermediates.

Suitable solvents are aliphatic or aromatic solvents such as hexane or toluene, ether solvents such as tetrahydrofuran or diethyl ether or halogenated hydrocarbons such as methylene chloride or halogenated aromatic hydrocarbons such as o-dichlorobenzene.

Biscyclopentadienyl compounds of the formula IV in which at least one of the radicals $R^3$ to $R^6$ and at least one of the radicals $R^7$ to $R^9$ is hydrogen and at least one of the radicals $R^3$ to $R^9$ is different from hydrogen can be reacted by literature methods to give the fulvenes of the formula IVb or IVc. This is illustrated by the following reaction scheme, where $R^{16}$, $R^{17}$, $R^{19}$ and $R^{20}$ are identical or different and are as defined for $R^{10}$.

-continued

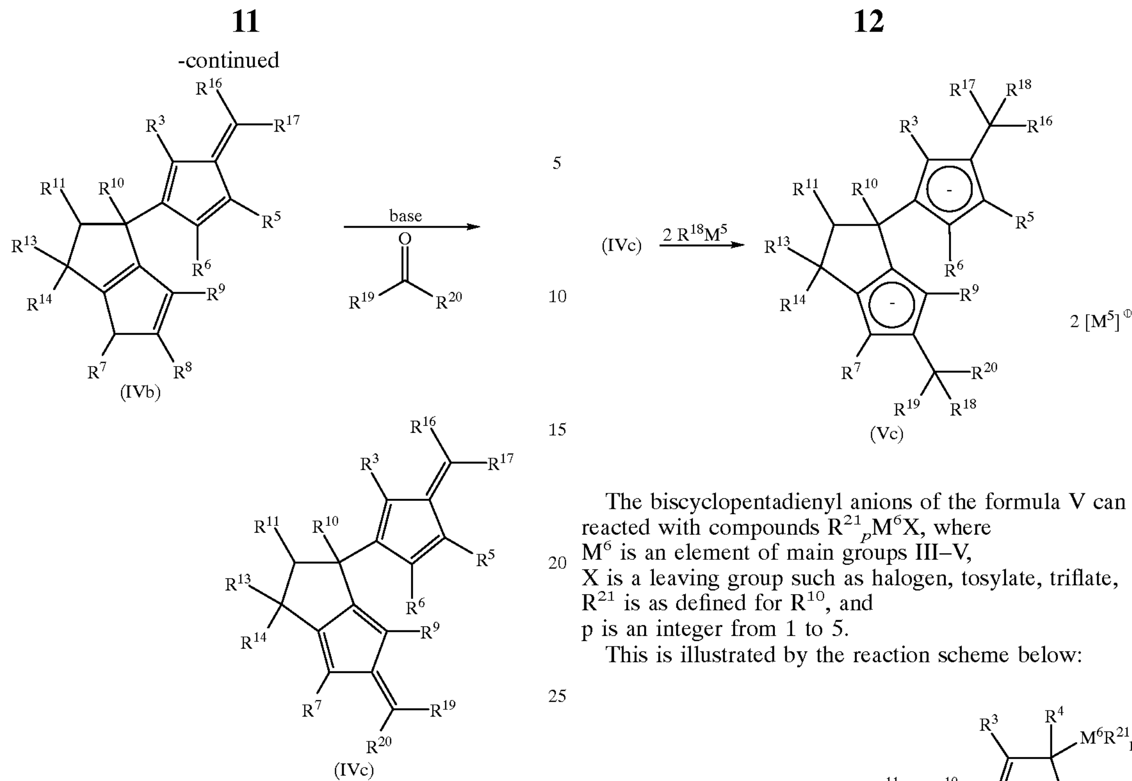

Reaction of the fulvene IVb with organometallic compounds of the formula $R^{18}M^5$ (where $R^{16}$, $R^{17}$, $R^{18}$, $R^{19}$ and $R^{20}$ are identical or different and are as defined for $R^{10}$; $M^5$ is as defined for $M^4$) leads to formation of the monoanion compound III. The use of two equivalents of $R^{18}M^5$ leads directly to formation of the dianion compound Vb.

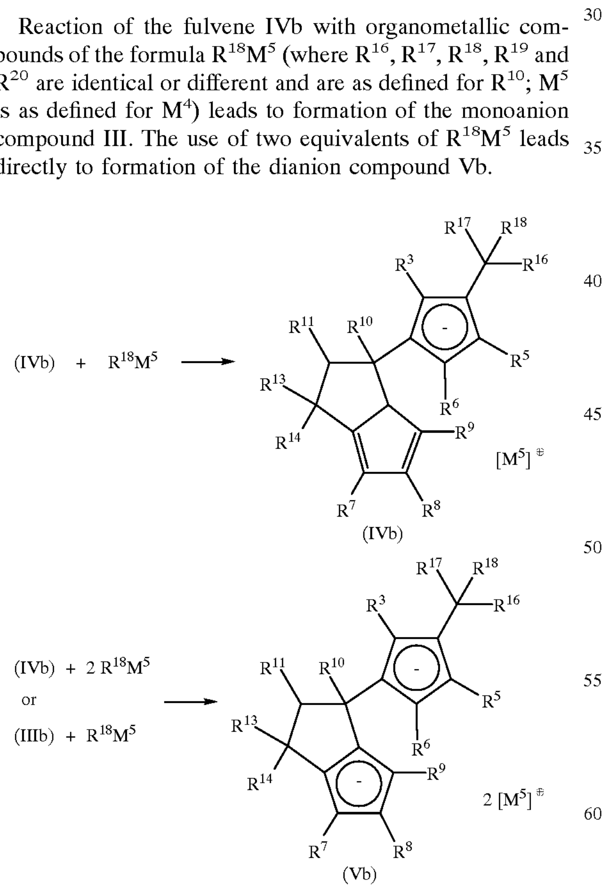

The reaction of the fulvene IVc leads, in a corresponding manner to the reaction of IVa, to formation of the dianion compound Vc.

The biscyclopentadienyl anions of the formula V can be reacted with compounds $R^{21}{}_pM^6X$, where $M^6$ is an element of main groups III–V, X is a leaving group such as halogen, tosylate, triflate, $R^{21}$ is as defined for $R^{10}$, and p is an integer from 1 to 5.

This is illustrated by the reaction scheme below:

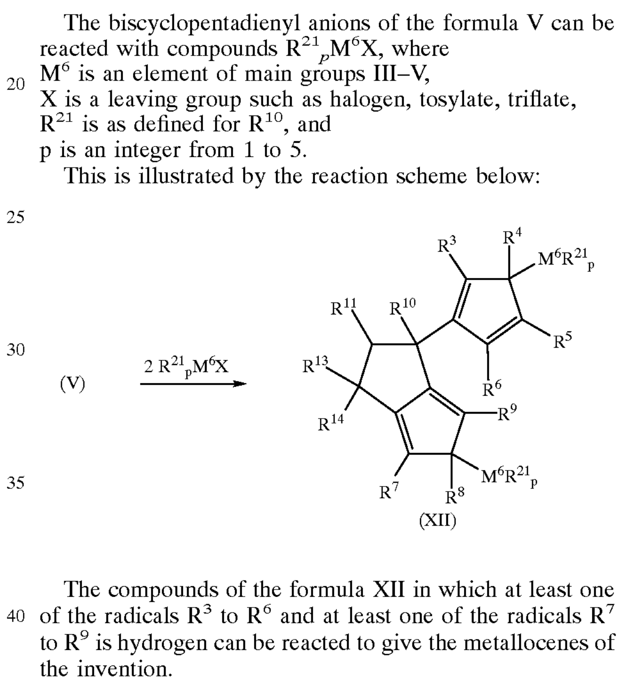

The compounds of the formula XII in which at least one of the radicals $R^3$ to $R^6$ and at least one of the radicals $R^7$ to $R^9$ is hydrogen can be reacted to give the metallocenes of the invention.

$R^{12}$ in the compounds of the formulae IIb, III, IV, V, VI, X, XI, Va, VIa, IVb, IVc, Vb, Vc and XII is hydrogen. $R^{14}$ in the compounds of the formulae X, XI, Va and VIa is hydrogen. The salts of the formula IIIb can be converted directly into the corresponding dianion compounds of the formula Va by deprotonation with, for example, butyllithium. The reaction to give the bridged metallocenes of the formula I is carried out in a corresponding manner to the reaction of V to give VI.

The metallocenes of the invention are highly active catalyst components for olefin polymerization. Depending on the substitution pattern of the ligands, the metallocenes can be formed as an isomer mixture. The metallocenes are preferably used as pure isomers. The use of the racemate is sufficient in most cases.

However, it is also possible to use the pure enantiomer in the (+) or (−) form. The pure enantiomers enable preparation of an optically active polymer. However, the configurationally isomeric forms of the metallocenes should be separated off, since the polymerization-active center (the metal atom) in these compounds produces a polymer having different properties. For certain applications, for example flexible moldings, this can be quite desirable.

The present invention also provides a process for preparing a polyolefin by polymerization of at least one olefin in the presence of a catalyst comprising at least one cocatalyst and at least one stereorigid metallocene compound having as ligands at least two substituted or unsubstituted cyclopentadienyl groups which are connected to one another via a five-membered ring, where at least one cyclopentadienyl group is fused onto the connecting five-membered ring. The term polymerization encompasses both homopolymerization and copolymerization.

In determining the number of ring atoms in the connecting five-membered ring of the metallocene compound used in the process of the invention, those carbon atoms of the cyclopentadienyl group fused onto the connecting five-membered ring which are, owing to the fusion, part of the connecting five-membered ring are also counted. Possible substituents on the connecting five-membered ring are not counted here.

Preferably, there is a cyclopentadienyl group of the metallocene compound used in the process of the invention as substituent on the connecting five-membered ring (i.e. the cyclopentadienyl group is bonded via a covalent bond to the connecting five-membered ring), while a further cyclopentadienyl group is fused onto the connecting five-membered ring. The cyclopentadienyl groups can be unsubstituted or substituted. The cyclopentadienyl group fused onto the connecting five- membered ring is preferably unsubstituted.

Substituted cyclopentadienyl groups preferably bear one or more $C_1$–$C_{30}$-radicals such as $C_1$–$C_{10}$-alkyl, $C_6$–$C_{20}$-aryl (e.g. phenyl or naphthyl) or two or more of the $C_1$–$C_{30}$-radicals form a ring system.

Examples of substituted cyclopentadienyl groups are methylcyclopentadienyl, methyl-tert-butylcyclopentadienyl, tert-butylcyclopentadienyl, isopropylcyclopentadienyl, dimethylcyclopentadienyl, trimethylethylcyclopentadienyl, phenylcyclopentadienyl, diphenylcyclopentadienyl, indenyl, methylindenyl, ethylindenyl, tert-butylindenyl, trimethylsilylindenyl, methylphenylindenyl, ethylphenylindenyl, methylnaphthylindenyl, methylisopropylindenyl, benzoindenyl, methyl-4,5-benzoindenyl, methyl-a-acenaphthindenyl, methyldiisopropylindenyl, fluorenyl, methylfluorenyl or di-tert- butylfluorenyl.

The connecting five-membered ring of the metallocene compound used in the process of the invention is preferably aliphatic and can also contain heteroatoms such as nitrogen, oxygen, sulfur, silicon or germanium. The connecting five-membered ring can also bear substituents such as $C_1$–$C_{40}$-groups (e.g. $C_1$–$C_{10}$-alkyl or $C_6$–$C_{20}$-aryl).

The central unit $M^1R^x{}_n$ of the metallocene compound used in the process of the invention preferably consists of a transition metal atom $M^1$, particularly from group IIIb, IVb, Vb or VIb of the Periodic Table of the Elements, which bears n substituents $R^x$ which are identical or different and are preferably each a $C_1$–$C_{40}$-group, a halogen atom, an OH group or a hydrogen atom. The sum of the number of substituents $R^x$ and the number of the substituted or unsubstituted cyclopentadienyl groups (ligands) corresponds to the valence of the transition metal atom $M^1$.

In the process of the invention, preference is given to using a stereorigid metallocene compound of the formula I (I)

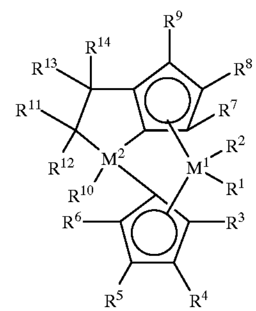

where $M^1$ is a metal of group IIIb, IVb, Vb or VIb of the Periodic Table, $M^2$ is carbon, silicon or germanium, $R^1$ and $R^2$ are identical or different and are each a hydrogen atom, a $C_1$–$C_{40}$-group such as a $C_1$–$C_{10}$-alkyl group, a $C_1$–$C_{10}$-alkoxy group, a $C_6$–$C_{10}$-aryl group, a $C_6$–$C_{25}$-aryloxy group, a $C_2$–$C_{10}$-alkenyl group, a $C_7$–$C_{40}$-arylalkyl group or a $C_7$–$C_{40}$-arylalkenyl group, an OH group, a halogen atom or $NR^{15}{}_2$, where $R^{15}$ are identical or different and are each a halogen atom, a $C_1$–$C_{10}$-alkyl group or a $C_6$–$C_{10}$-aryl group or form a ring system, or $R^1$ and $R^2$ together with the atoms connecting them form a ring system, $R^3$, $R^4$, $R^5$, $R^6$, $R^7$, $R^8$ and $R^9$ are identical or different and are each a hydrogen atom, a halogen atom, a $C_1$–$C_{40}$-group such as a $C_1$–$C_{10}$-alkyl group which can be halogenated, a $C_6$–$C_{20}$-aryl group which can be halogenated, a $C_6$–$C_{20}$-aryloxy group, a $C_2$–$C_{12}$-alkenyl group, a $C_7$–$C_{40}$-arylalkyl group, a $C_7$–$C_{40}$-alkylaryl group or a $C_8$–$C_{40}$-arylalkenyl group, an —$SiR^{15}{}_3$, —$NR^{15}{}_2$—, —$SiOR^{15}{}_3$—, —$SiSR^{15}{}_3$— or —$PR^{15}{}_2$ radical, where $R^{15}$ are identical or different and are each a halogen atom, a $C_1$–$C_{10}$-alkyl group or a $C_6$–$C_{10}$-aryl group or form a ring system, or two or more adjacent radicals $R^3$, $R^4$, $R^5$, $R^6$, $R^7$, $R^8$ and $R^9$ together with the atoms connecting them form a ring system which preferably contains from 4 to 40, particularly preferably from 6 to 20, carbon atoms, $R^{10}$ is a hydrogen atom or a $C_1$–$C_{40}$-group such as a $C_1$–$C_{20}$-alkyl group, a $C_1$–$C_{10}$-alkoxy group, a $C_6$–$C_{20}$-aryl group, a $C_6$–$C_{20}$-aryloxy group, a $C_2$–$C_{12}$-alkenyl group, a $C_7$–$C_{40}$-arylalkyl group, a $C_7$–$C_{40}$-alkylaryl group or a $C_8$–$C_{40}$-arylalkenyl group, which can each bear radicals —$NR^{15}{}_3$, —$SiR^{15}{}_3$, —$SR^{15}{}_2$ or —$OSiR^{15}{}_3$, where $R^{15}$ is a halogen atom, a $C_1$–$C_{10}$-alkyl group or a $C_6$–$C_{10}$-aryl group, or $R^{10}$ is connected to one or more of the radicals $R^3$, $R^4$, $R^5$ and $R^6$, $R^{11}$ and $R^{12}$ are identical or different and are each a hydrogen atom, a $C_1$–$C_{40}$-group such as a $C_1$–$C_{20}$-alkyl group, a $C_1$–$C_{10}$-alkoxy group, a $C_6$–$C_{20}$-aryl group, a $C_2$–$C_{12}$-alkenyl group, a $C_7$–$C_{40}$-arylalkyl group, a $C_7$–$C_{40}$-alkylaryl group or a $C_8$–$C_{40}$-arylalkenyl group, which can each bear radicals such as a halogen atom, —$NR^{15}{}_3$, —$SR^{15}{}_3$, —$SiR^{15}{}_3$ or —$OSiR^{15}{}_3$, where $R^{15}$ is a halogen atom, a $C_1$–$C_{10}$-alkyl group or a $C_6$–$C_{10}$-aryl group, $R^{13}$ and $R^{14}$ are identical or different and are each a hydrogen atom, a $C_1$–$C_{40}$-group such as a $C_1$–$C_{20}$-alkyl group, a $C_1$–$C_{10}$-alkoxy group, a $C_6$–$C_{20}$-aryl group, a $C_2$–$C_{12}$-alkenyl group, a $C_7$–$C_{40}$-arylalkyl group, a $C_7$–$C_{40}$-alkylaryl group or a $C_8$–$C_{40}$-arylalkenyl group, which can each bear radicals such as a halogen atom, —$NR^{15}_3$, —$SR^{15}_2$, —$SiR^{15}_3$ or —$OSiR^{15}_3$, where $R^{15}$ is a halogen atom, a $C_1$–$C_{10}$-alkyl group or a $C_6$–$C_{10}$-aryl group.

For compounds of the formula I, it is preferred that $M^1$ is a metal of group IVb of the Periodic Table of the Elements such as titanium, zirconium or hafnium, in particular zirconium, $R^1$ and $R^2$ are identical and are each a $C_1$–$C_4$-alkyl group or a halogen atom such as fluorine, chlorine, bromine or iodine, in particular chlorine, $R^3$, $R^4$, $R^5$, $R^6$, $R^7$, $R^8$ and $R^9$ are identical or different and are each a hydrogen atom, a $C_1$–$C_{10}$-alkyl group or a $C_6$–$C_{24}$-aryl group, or two or more adjacent radicals $R^3$, $R^4$, $R^5$, $R^6$, $R^7$, $R^8$ and $R^9$ together with the atoms connecting them form an aromatic or aliphatic ring system having from 4 to 20 carbon atoms, $R^{10}$ is a hydrogen atom, a $C_6$–$C_{24}$-aryl group or a $C_1$–$C_{10}$-alkyl group, in particular a $C_1$–$C_4$-alkyl group, $M^2$ is carbon, $R^{11}$ and $R^{12}$ are identical or different and $R^{11}$ is a hydrogen atom, a $C_1$–$C_{10}$-group, in particular a $C_1$–$C_4$-alkyl group or a $C_6$–$C_{10}$-aryl group and $R^{12}$ is a hydrogen atom and $R^{13}$ and $R^{14}$ are identical or different and are each a hydrogen atom, a $C_1$–$C_{10}$-group, in particular a $C_1$–$C_4$-alkyl group or a $C_6$-$C_{10}$-aryl group.

Particular preference is given to compounds of the formula I in which $M^1$ is zirconium, $R^1$ and $R^2$ are identical and are each a halogen atom, in particular chlorine, $R^3$, $R^4$, $R^5$, $R^6$, $R^7$ and $R^9$ are identical or different and are each a hydrogen atom or a $C_1$–$C_4$-alkyl group such as methyl, ethyl, propyl, isopropyl, butyl or isobutyl or a $C_6$–$C_{14}$-aryl group such as phenyl or naphthyl, or $R^3$ and $R^4$ and/or $R^5$ and $R^6$ together with the atoms connecting them form an aromatic hydrocarbon ring system having from 4 to 20 carbon atoms, in particular a six-membered ring which in turn can be substituted, $R^8$ is a hydrogen atom, $M^2$ is a carbon atom, $R^{10}$ is a hydrogen atom, a $C_1$–$C_6$-alkyl group, in particular methyl, or a $C_6$–$C_{10}$-aryl group, in particular phenyl, $R^{11}$ and $R^{12}$ are identical and are each a hydrogen atom and $R^{13}$ and $R^{14}$ are identical or different and are each a methyl or a phenyl group.

In the process of the invention, particular preference is given to using a stereorigid metallocene compound having a ligand system which is different from 4-[$\eta^5$-3'-alkylcyclopentadienyl)-4,6,6-trimethyl-($\eta^5$-2-alkyl-4,5-tetrahydropentalene]. When $M^2$ is carbon and $R^{10}$, $R^{13}$ and $R^{14}$ are methyl it is preferred that at least one of the radicals $R^3$, $R^5$, $R^6$, $R^7$ and $R^9$ is different from hydrogen and/or $R^3$ is hydrogen.

In the process of the invention, preference is given to polymerizing one or more olefins of the formula $R^a$—CH═CH—$R^b$, where $R^a$ and $R^b$ are identical or different and are each a hydrogen atom or a hydrocarbon radical having from 1 to 20 carbon atoms, in particular from 1 to 10 carbon atoms, and Ra and Rb together with the atoms connecting them can form one or more rings. Examples of such olefins are 1-olefins having from 2 to 40, preferably 2–10, carbon atoms, for example ethylene, propylene, 1-butene, 1-pentene, 1-hexene, 4-methyl-1-pentene or 1-octene, styrene, dienes such as 1,3-butadiene, isoprene, 1,4-hexadiene or cyclic olefins.

In the process of the invention, preference is given to homopolymerizing ethylene or propylene, or copolymerizing ethylene with one or more acyclic 1-olefins having from 3 to 20 carbon atoms, for example propylene, and/or one or more dienes having from 4 to 20 carbon atoms, for example 1,3-butadiene. Examples of such copolymers are ethylene-propylene copolymers and ethylene-propylene-1,4-hexadiene copolymers.

The polymerization is preferably carried out at a temperature of from −60 to 250° C., particularly preferably from 50 to 200° C. The pressure is preferably from 0.5 to 2000 bar, particularly preferably from 5 to 64 bar.

The polymerization can be carried out in solution, in bulk, in suspension or in the gas phase, continuously or batchwise, in one or more stages. Preferred embodiments are gas-phase and solution polymerization.

The catalyst used in the process of the invention preferably contains one metallocene compound. It is also possible to use mixtures of two or more metallocene compounds, eg. for preparing polyolefins having a broad or multimodal molecular weight distribution.

In principle, a suitable cocatalyst in the process of the invention is any compound which, owing to its Lewis acidity, can convert the neutral metallocene into a cation and stabilize the latter ("labile coordination").

Furthermore, the cocatalyst or the anion formed therefrom should undergo no further reactions with the metallocene cation formed (EP 427 697). As cocatalyst, preference is given to using an aluminum compound and/or a boron compound.

The boron compound preferably has the formula $R^{22}_xNH_{4-x}BR^{23}_4$, $R^{22}_xPH_{4-x}BR^{23}_4$, $R^{22}_3CBR^{23}_4$ or $BR^{23}_3$, where x is a number from 1 to 4, preferably 3, the radicals $R^{22}$ are identical or different, preferably identical, and are $C_1$–$C_{10}$-alkyl or $C_6$–$C_{18}$-aryl, or two radicals $R^{22}$ together with the atoms connecting them form a ring, and the radicals $R^{23}$ are identical or different, preferably identical, and are $C_6$–$C_{18}$-aryl which can be substituted by alkyl, haloalkyl or fluorine. In particular, $R^{22}$ is ethyl, propyl, butyl or phenyl and $R^{23}$ is phenyl, pentafluorophenyl, 3,5-bistrifluoromethylphenyl, mesityl, xylyl or tolyl (EP 277 003, EP 277 004 and EP 426 638).

The cocatalyst used is preferably an aluminum compound such as aluminoxane and/or an aluminum alkyl.

The cocatalyst used is particularly preferably an aluminoxane, in particular of the formula XIIIa for the linear type and/or of the formula XIIIb for the cyclic type, (XIIIa)

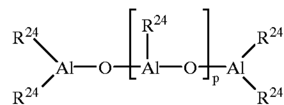

(XIIIb)

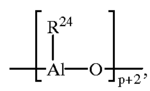

where, in the formulae XIIIa and XIIIb, the radicals $R^{24}$ are identical or different and are each hydrogen or a $C_1C_{20}$-hydrocarbon group such as a $C_1$–$C_{18}$-alkyl group, a $C_6$–$C_{18}$-aryl group or benzyl, and p is an integer from 2 to 50, preferably from 10 to 35.

The radicals $R^{24}$ are preferably identical and are hydrogen, methyl, isobutyl, phenyl or benzyl, particularly preferably methyl.

If the radicals $R^{24}$ are different, they are preferably methyl and hydrogen or alternatively methyl and isobutyl, where hydrogen or isobutyl is preferably present in a numerical proportion of from 0.01 to 40% (of the radicals $R^{24}$).

The methods of preparing the aluminoxanes are known. The exact spatial structure of the aluminoxanes is not known (J. Am. Chem. Soc. (1993) 115, 4971). For example, it is conceivable that chains and rings join to form larger two-dimensional or three-dimensional structures.

Regardless of the method of preparation, all aluminoxane solutions have in common a varying content of unreacted aluminum starting compound which is present in free form or as adduct.

It is possible to preactivate the metallocene compound with a cocatalyst, in particular an aluminoxane, prior to use in the polymerization reaction. This significantly increases the polymerization activity. The preactivation of the metallocene compound is preferably carried out in solution. Here, the metallocene compound is preferably dissolved in a solution of the aluminoxane in an inert hydrocarbon. Suitable inert hydrocarbons are aliphatic or aromatic hydrocarbons. Preference is given to using toluene.

The concentration of the aluminoxane in the solution is in the range from about 1% by weight to the saturation limit, preferably from 5 to 30% by weight, in each case based on the total amount of solution. The metallocene can be used in the same concentration, but it is preferably used in an amount of from $10^{-4}$ to 1 mol per mol of aluminoxane. The preactivation time is from 5 minutes to 60 hours, preferably from 5 to 60 minutes. The preactivation is carried out at a temperature of from −78 to 100° C., preferably from 0 to 80° C.

The metallocene compound is preferably used in a concentration, based on the transition metal, of from $10^{-3}$ to $10^{-8}$ mol, preferably from $10^{-4}$ to $10^{-7}$ mol, of transition metal per $dm^3$ of solvent or per $dm^3$ of reactor volume. The aluminoxane is preferably used in a concentration of from $10^{-6}$ to $10^{-1}$ mol, preferably from $10^{-5}$ to $10^{-2}$ mol, per $dm^3$ of solvent or per $dm^3$ of reactor volume. The other cocatalysts mentioned are used in approximately equimolar amounts to the metallocene compound. However, higher concentrations are also possible in principle.

The aluminoxane can be prepared in various ways by known methods. One of the methods is, for example, reacting an aluminum-hydrocarbon compound and/or a hydridoaluminum-hydrocarbon compound with water (gaseous, solid, liquid or bound—for example as water of crystallization) in an inert solvent (for example toluene). To prepare an aluminoxane having different radicals $R^{24}$, for example, two different trialkylaluminums corresponding to the desired composition are reacted with water.

To remove catalyst poisons present in the olefin, purification using an aluminum compound, preferably an aluminum alkyl such as trimethylaluminum or triethylaluminum, is advantageous. This purification can be carried out either in the polymerization system itself or the olefin is, prior to addition to the polymerization system, brought into contact with the aluminum compound and subsequently separated off again.

As molecular weight regulator and/or to increase the catalyst activity, hydrogen can be added in the process of the invention. This enables low molecular weight polyolefins such as waxes to be obtained.

In the process of the invention, the metallocene compound is preferably reacted with the cocatalyst outside the polymerization reactor in a separate step using a suitable solvent. Application to a support can be carried out during the step.

A prepolymerization can be carried out in the process of the invention by means of the metallocene compound. For the prepolymerization, preference is given to using the (or one of the) olefin(s) used in the polymerization.

The catalyst used in the process of the invention can be supported. The application to a support enables, for example, the particle morphology of the polyolefin prepared to be controlled. Here, the metallocene compound can be reacted first with the support and subsequently with the cocatalyst. The cocatalyst can also first be supported and subsequently reacted with the metallocene compound. It is also possible to support the reaction product of metallocene compound and cocatalyst. Suitable support materials are, for example, silica gels, aluminum oxides, solid aluminoxane or other inorganic support materials such as magnesium chloride. Another suitable support material is a polyolefin powder in finely divided form. The preparation of the supported cocatalyst can, for example, be carried out as described in EP 567 952.

The cocatalyst, e.g. aluminoxane, is preferably applied to a support such as silica gels, aluminum oxides, solid aluminoxane, other inorganic support materials or a polyolefin powder in finely divided form and then reacted with the metallocene.

Inorganic supports used can be oxides which have been produced flame-pyrolytically by combustion of element halides in a hydrogen/oxygen flame, or can be prepared as silica gels in certain particle size distributions and particle shapes.

The preparation of the supported cocatalyst can be carried out, for example as described in EP 578 838, in the following manner in a stainless steel reactor having an explosion-proof design and provided with a pumped circulation system having a pressure rating of 60 bar, inert gas supply and temperature control by jacket cooling and a second cooling circuit via a heat exchanger on the pumped circulation system. The pumped circulation system sucks in the reactor contents via a connection in the bottom of the reactor by means of a pump and forces it into a mixer and through an ascending line via a heat exchanger back into the reactor. The mixer is configured in such a way that in the inlet there is located a constricted tube cross section where an increased flow velocity occurs and into whose turbulent zone there is led, axially and counter to the flow direction, a thin feed line through which, pulsed, a defined amount of water under 40 bar of argon can be fed in. The reaction is monitored via a sampler on the pumped circuit.

However, other reactors are also suitable in principle.

The above described reactor having a volume of 16 $dm^3$ is charged with 5 $dm^3$ of decane under inert conditions. 0.5 $dm^3$ (=5.2 mol) of trimethylaluminum are added at 25° C. Subsequently, 250 g of silica gel SD 3216-30 (Grace AG) which were dried beforehand at 120° C. in an argon fluidized bed are metered into the reactor through a solids funnel and homogeneously distributed by means of the stirrer and the pumped circulation system. A total amount of 76.5 g of water is added to the reactor in portions of 0.1 $cm^3$ every 15 seconds over a period of 3.25 hours. The pressure, resulting from the argon and the gases evolved, is kept constant at 10 bar by means of a pressure regulating valve. After all the water has been introduced, the pumped circulation system is switched off and stirring is continued for a further 5 hours at 25° C.

The supported cocatalyst prepared in this way is used as a 10% strength suspension in n-decane. The aluminum content is 1.06 mmol of Al per $cm^3$ of suspension. The isolated solid contains 31% by weight of aluminum, the suspension medium contains 0.1% by weight of aluminum.

Further possible ways of preparing a supported cocatalyst are described in EP 578 838.

The metallocene of the invention is then applied to the supported cocatalyst by stirring the dissolved metallocene with the supported cocatalyst. The solvent is removed and replaced by a hydrocarbon in which both cocatalyst and the metallocene are insoluble.

The reaction to form the supported catalyst system is carried out at a temperature of from —20 to +120° C., preferably from 0 to 100° C., particularly preferably at from 15 to 40° C. The metallocene is reacted with the supported cocatalyst by combining the cocatalyst as a 1–40% strength by weight suspension, preferably a 5–20% strength by weight suspension, in an aliphatic, inert suspension medium such as n-decane, hexane, heptane or diesel oil with a solution of the metallocene in an inert solvent such as toluene, hexane, heptane or dichloromethane or with the finely milled solid of the metallocene. The other way around, it is also possible to react a solution of the metallocene with the solid of the cocatalyst.

The reaction is carried out by intensive mixing, for example by stirring, at a molar $Al/M^1$ ratio of from 100/1 to 10,000/1, preferably from 100/1 to 3000/1, and a reaction time of from 5 to 120 minutes, preferably from 10 to 60 minutes, particularly preferably from 10 to 30 minutes, under inert conditions.

Over the course of the reaction time for preparing the supported catalyst system, changes in the color of the reaction mixture occur, particularly when using metallocenes of the invention having absorption maxima in the visible region, and the progress of the reaction can be followed by means of these changes.

After the reaction time has elapsed, the supernatant solution is separated off, for example by filtration or decantation. The solid which remains is washed from 1 to 5 times with an inert suspension medium such as toluene, n-decane, hexane, diesel oil or dichloromethane for removing soluble constituents in the catalyst formed, in particular for removing unreacted and therefore soluble metallocene.

The supported catalyst system thus prepared, either dried in vacuo as powder or still moist with solvent, can be resuspended and be metered into the polymerization system as a suspension in one of the abovementioned inert suspension media.

If the polymerization is carried out as a suspension or solution polymerization, an inert solvent customary for the Ziegler low-pressure process is used. For example, the polymerization is carried out in an aliphatic or cycloaliphatic hydrocarbon; examples of such hydrocarbons which may be mentioned are propane, butane, hexane, heptane, isooctane, cyclohexane and methylcyclohexane. It is also possible to use a petroleum or hydrogenated diesel oil fraction. Toluene can also be used. Preference is given to carrying out the polymerization in the liquid monomer.

Prior to addition of the catalyst, in particular the supported catalyst system (comprising the metallocene of the invention and a supported cocatalyst), another aluminum alkyl compound such as trimethylaluminum, triethylaluminum, triisobutylaluminum, trioctylaluminum or isoprenylaluminum can additionally be added to the reactor to make the polymerization system inert (for example to remove catalyst poisons present in the olefin). This is added to the polymerization system in a concentration of from 100 to 0.01 mmol of Al per kg of reactor contents. Preference is given to triisobutylaluminum and triethylaluminum in a concentration of from 10 to 0.1 mmol of Al per kg of reactor contents. This makes it possible to select a small molar $Al/M^1$ratio in the synthesis of a supported catalyst sytem.

If inert solvents are used, the monomers are metered in in gaseous or liquid form.

The polymerization time can be any desired, since the catalyst system to be used in the process of the invention shows only a slight time-dependent decrease in the polymerization activity.

The specific stereorigid metallocene compounds described in the present invention are suitable for preparing polyolefins, in particular those having reduced crystallinity, increased impact toughness, increased transparency, high flowability at processing temperatures and also a reduced melting point.

Main applications of such polyolefins are plasticizer and lubricant formulations, melt adhesive applications, coatings, seals, insulation, filling compositions or sound insulation materials.

Use of hydrogen or increasing the polymerization temperature also makes it possible to obtain polyolefins of low molecular weight, for example waxes, whose hardness or melting point can be varied by means of the comonomer content.

The other way around, selection of the polymerization conditions also enables the preparation of high molecular weight polyolefins which are suitable as thermoplastic materials. These are suitable, in particular, for producing shaped bodies such as films, plates or large hollow bodies (e.g. tubes).

Selection of the polymerization process and the comonomer type(s), and also the amount(s) of comonomer(s), enables the preparation of olefin copolymers having elastomeric properties, e.g. ethylene-propylene-1,4-hexadiene terpolymers.

The examples below illustrate the invention.

Preparation and handling of organometallic compounds were carried out with exclusion of air and moisture under argon protective gas (Schlenk technique). All solvents required were made absolute prior to use by boiling for a number of hours over a suitable dessicant and subsequent distillation.

The α,β-unsaturated ketones and fulvenes used as starting compounds were prepared by literature methods (Synleft 771 (1991); J. Chem. Soc., Commun. 1694 (1986); Chem. Ber. 116, 119 (1983); Tetrahedron Lett. 23; 1447 (1982)), cyclopentadiene and methylcyclopentadiene were obtained by cracking of the dimers and were stored at −35° C.

The $Al/CH_3$ ratio in the aluminoxane was determined by decomposing the sample with $H_2SO_4$ and determining the volume of the hydrolysis gases formed at STP and also by complexometric titration of the aluminum in the then completely dissolved sample by the Schwarzenbach method.

The compounds were characterized using 1H-NMR, $^{13}C$-NMR and IR spectroscopy.

The polymer melting points and heats of fusion given are taken from a DSC measurement for the 2nd melting at a heating rate of 10°/min.

For comparative examples, toluene-soluble methylaluminoxane is sourced as a 10% strength toluene solution from Witco and, according to an aluminum determination, contains 36 mg of Al/ml.

The comonomer incorporation is determined using $^{13}C$-NMR according to the method of Randall (Macromolecules 27, 2120 (1994)).

Definitions:

VN=Viscosity number in $cm^3/g$ $M_w$=Weight average molecular weight in g/mol (determined by gel permeation chromatography)

$M_w/M_n$=Polydispersity mp.=Melting point in °C. (determined using DSC, 20° C./min heating and cooling rate)

II=Isotactic index (II=mm+½ mr, determined by $^{13}$C-NMR spectroscopy)

MFI 230/5=Melt flow index measured in accordance with DIN 53735; in dg/min

BD=Polymer bulk density in g/dm$^3$

A. [4-(h$^5$-Indenyl)-4-methyl-6-phenyl-(h$^5$-4,5-tetrahydropentalene)]-dichlorozirconium 1. 4-Methyl-6-phenyl-5,6-dihydropentalene 208 g (359 mmol) of pyrrolidine are added dropwise at 0° C. over a period of 45 minutes to a mixture of 35.0 g (239 mmol) of benzalacetone and 38.1 g (717 mmol) of cyclopentadiene in 300 ml of methanol. The red reaction solution is stirred for 40 minutes at room temperature and is subsequently admixed at 0° C. with 19 g (346 mmol) of glacial acetic acid. After addition of 300 ml of water and 500 ml of diethyl ether, the product is extracted. The aqueous phase is extracted twice with 250 ml each time of diethyl ether, the combined ether phases are dried over $MgSO_4$ and the solvent is removed under reduced pressure. The crude product is distilled in an oil pump vacuum, giving 24.1 g (52%) of 4-methyl-6-phenyl-5,6-dihydropentalene.

2. 4-Indenyl-4-methyl-6-phenyl-4,5-tetrahydropentalene

A solution of 12.6 g (103 mmol) of indenyllithium in 40 ml of tetrahydrofuran is added dropwise at room temperature to a solution of 20.0 g (103 mmol) of 4-methyl-6-phenyl-5,6-dihydropentalene in 75 ml of tetrahydrofuran. The reaction solution is stirred for 24 hours at room temperature and subsequently refluxed for a further 6 hours. The reaction is stopped by addition of water. The product is extracted with diethyl ether, the aqueous phase is washed twice with 50 ml each time of diethyl ether and the combined organic phases are dried over $MgSO_4$. Removal of the solvent under reduced pressure and subsequent chromatography (eluant: hexane/dichloromethane: 20/1) gives 17.5 g (55%) of 4-indenyl-4-methyl-6-phenyl-4,5-tetrahydropentalene.

$^1$H-NMR (200 MHz, $CDCl_3$): 8.4–7.3 (m, 9H, arom. H), 6.8–5.9 (m, 4H, H—C(2'), H—C(1–3)), 3.4–3.2 (m, 2H, H—C(4), H—C(7)), 2.4–1.8 (m, 5H, H—C(3'), H—C(5), H—C(6)), 1.6 (s, 3H, $CH_3$).

3. [4-($\eta^5$-Indenyl)-4-methyl-6-phenyl-($\eta^5$-4,5-tetrahydropentalene)]-dichlorozirconium 42.5 ml (68 mmol) of a 1.6 molar butyllithium solution in hexane are added dropwise to a solution of 10.5 g (34 mmol) of 4-indenyl-6-phenyl-4,5-tetrahydropentalene in 50 ml of tetrahydrofuran. The solution is stirred for a further 3 hours, subsequently cooled to −78° C. and admixed with 4.1 g (17 mmol) of zirconium tetrachloride added in portions. The solution is stirred for 24 hours and the solvent is subsequently removed under reduced pressure. The product is extracted with 125 ml of dichloromethane, the solution is evaporated to a volume of 25 ml and 4.4 g (55%) of [4-($\eta^5$-indenyl)-4-methyl-6-phenyl-($\eta^5$-4,5-tetrahydropentalene)]dichlorozirconium are obtained in the form of a yellow powder.

$^1$H-NMR (200 MHz, $CDCl_3$): 8.3–7.2 (m, 9H, arom. H), 6.8–5.7 (m, 5H, H—C(2'), H—C(3'), H—C(1–3)), 3.5 (m, 1H, H—C(4)), 2.2–1.9 (m, 3H, H—C(5), H—C(6)), 1.7 (s, 3H, $CH_3$). Mass spectrum: 468 M$^+$, correct disintegration pattern.

B. [4-($\eta^5$-Cyclopentadienyl)-4,6-diphenyl-($\eta^5$-4,5-tetrahydropentalene)]dichlorozirconium 1. 4,6-Diphenyl-5,6-dihydropentalene 230 g (324 mmol) of pyrrolidine are added dropwise at 0° C. over a period of 45 minutes to a mixture of 45.0 g (216 mmol) of benzalacetophenone and 42.8 g (648 mmol) of cyclopentadiene in 350 ml of methanol. The red reaction solution is stirred for 40 minutes at room temperature and is subsequently admixed at 0° C. with 21 g (346 mmol) of glacial acetic acid. After addition of 300 ml of water and 500 ml of diethyl ether, the product is extracted. The aqueous phase is extracted twice with 250 ml each time of diethyl ether, the combined ether phases are dried over $MgSO_4$ and the solvent is removed under reduced pressure. The crude product is distilled in an oil pump vacuum, giving 30.5 g (55%) of 4,6-diphenyl-5,6-dihydropentalene.

2. 4-Cyclopentadienyl-4,6-diphenyl-4,5-tetrahydropentalene

A solution of 4.25 g (59 mmol) of cyclopentadienyllithium in 25 ml of tetrahydrofuran is added dropwise at room temperature to a solution of 15.0 g (59 mmol) of 4,6-diphenyl-5,6-dihydropentalene in 50 ml of tetrahydrofuran. The reaction solution is stirred for 24 hours at room temperature and subsequently refluxed for a further 6 hours. The reaction is stopped by addition of water. The product is extracted with diethyl ether, the aqueous phase is washed twice with 50 ml each time of diethyl ether and the combined organic phases are dried over $MgSO_4$. Removal of the solvent under reduced pressure and subsequent chromatography (eluant: hexane/dichloromethane: 20/1) gives 12.3 g (65%) of 4-cyclopentadienyl-4,6-diphenyl-4,5-tetrahydropentalene.

$^1$H-NMR (200 MHz, $CDCl_3$): 8.4–7.1 (m, 10H, arom. H), 6.9–5.7 (m, 6H, H—C(2'), H—C(3'), H—C(5—), H—C(1), H—C(2), H—C(3)), 3.3–3.1 (m, 2H, H—C(4), H—C(7)), 2.4–1.8 (m, 5H, H—C(5), H—C(6), H—C(4')).

3. [4-($\eta^5$-Cyclopentadienyl)-4,6-diphenyl-($\eta^5$-4,5-tetrahydropentalene)]dichlorozirconium 33 ml (53 mmol) of a 1.6 molar butyllithium solution in hexane are added dropwise to a solution of 8.5 g (26 mmol) of 4-cyclopentadienyl-4,6-diphenyl-4,5-tetrahydropentalene in 50 ml of tetrahydrofuran. The solution is stirred for a further 3 hours, subsequently cooled to −78° C. and admixed with 3.1 g (13 mmol) of zirconium tetrachloride added in portions. The solution is stirred for 24 hours and the solvent is subsequently removed under reduced pressure. The product is extracted with 100 ml of dichloromethane, the solution is evaporated to a volume of 25 ml and 5.6 g (45%) of [4-($\eta^5$-cyclopentadienyl)-4,6-diphenyl-($\eta^5$-4,5-tetrahydropentalene)]dichlorozirconium are obtained in the form of a yellow powder.

$^1$H-NMR (200 MHz, $CDCl_3$): 8.5–7.2 (m, 10H, arom. H), 6.8–5.6 (m, 7H, H—C(2'), H—C(3'), H—C(4'), H—C(5'), H—C(1), H—C(2), H—C(3)), 3.4 (m, 1H, H—C(4)), 2.4–1.8 (m, 3H, H—C(5), H—C(6)). Mass spectrum: 481 M$^+$, correct disintegration pattern.

C. [4-($\eta^5$-Indenyl)-($\eta^5$-4,5-tetrahydropentalene)] dichlorozirconium 1. 4-(Dimethylamino)-5,6-dihydropentalene A solution of 20.0 g (136 mmol) of (E)-6-[2-(dimethylamino)ethenyl]-fulvene in 100 ml of piperidine is boiled under reflux for 2 hours. The solvent is removed under reduced pressure and the residue is recrystallized from diethyl ether. This gives 12.5 g (63%) of 4-(dimethylamino)-5,6-dihydropentalene in the form of a yellow powder.

2. 4-Indenyl-5,6-dihydropentalene

A solution of 12.5 g (85 mmol) of 4-(dimethylamino)-5,6-dihydropentalene in 50 ml of tetrahydrofuran are admixed with a solution of 10.4 g (85 mmol) of indenyllithium in 20 ml of tetrahydrofuran. The reaction solution is stirred for 24 hours at room temperature and the reaction is stopped by addition of water. Extraction with diethyl ether, drying of the organic phases over $MgSO_4$ and removal of the solvent under reduced pressure and subsequent recrystallization of the crude product from diethyl ether gives 13.9 g (75%) of 4-indenyl-5,6-dihydropentalene.

$^1$H-NMR (200 MHz, $CDCl_3$): 7.7–7.2 (m, 4H, arom. H), 6.2–5.6 (m, 4H, olefin. H), 3.4–2.2 (m, 6H, aliphat. H).

3. 4-Indenyl-4,5-tetrahydropentalene

A solution of 12.0 g (55 mmol) of 4-indenyl-5,6-dihydropentalene in 40 ml of diethyl ether is added dropwise at room temperature to a suspension of 6.3 g (165 mmol) of lithium aluminum hydride in 150 ml of diethyl ether. The orange suspension is heated under reflux for three hours and subsequently to 0° C. The mixture is hydrolyzed with ice water and the white precipitate formed is filtered off and washed a number of times with a little diethyl ether. The combined ether phases are dried over $MgSO_4$ and the solvent is removed under reduced pressure. This gives 11.5 g (96%) of 4-indenyl-4,5-tetrahydropentalene as a yellow oil.

$^1$H-NMR (200 MHz, $CDCl_3$): 7.6–7.1 (m, 4H, arom. H), 6.3–5.7 (m, 4H, H—C(1), H—C(2), H—C(3), H—C(2')), 3.4–3.2 (m, 2H, H—C(4), H—C(7)), 2.8–2.2 (m, 6H, H—C(5), H—C(6), H—C(2')).

4. [4-($\eta^5$-Indenyl)-($\eta^5$-4,5-tetrahydropentalene)] dichlorozirconium 57 ml (92 mmol) of a 1.6 molar methyllithium solution in hexane are added dropwise to a solution of 10.0 g (46 mmol) of 4-indenyl-4,5-tetrahydropentalene in 50 ml of toluene. The solution is stirred for a further 3 hours. The suspension formed is cooled to −78° C. and subsequently admixed with 5.4 g (23 mmol) of zirconium tetrachloride added in portions. The suspension is stirred for 24 hours and subsequently filtered through a G3 frit. The residue is further extracted with 100 ml of toluene and the combined toluene filtrates are freed of the solvent under reduced pressure. This gives 3.5 g (40%) of [4-($\eta^5$-indenyl)-($\eta^5$-4,5-tetrahydropentalene)]dichlorozirconium in the form of a yellow powder.

$^1$H-NMR (200 MHz, $CDCl_3$): 7.5–7.1 (m, 4H, arom. H), 6.4–5.7 (m, 5H, H—C(1), H—C(2), H—C(3), H—C(2'), H—C(5'), 3.3 (m, 1H, H—C(4)), 2.8–2.2 (m, 4H, H—C(5), H—C(6)). Mass spectrum: 380 $M^+$, correct disintegration pattern.

What is claimed is:

1. 4-($\eta^5$-indenyl)-4-methyl-6-phenyl-($\eta^5$-4,5-tetrahydropentalene)-dichloro zirconium.

2. A metallocene is selected from the group consisting of

[4-($\eta^5$-cyclopentadienyl)($\eta^5$-4,5-tetrahydropentalene)] dichlorotitanium, [4-($\eta^5$-cyclopentadienyl)($\eta^5$-4,5-tetrahydropentalene)]dichlorozirconium, [4-($\eta^5$-cyclopentadienyl)($\eta^5$-4,5-tetrahydropentalene)] dichlorohafnium,

[4-($\eta^5$-cyclopentadienyl)-4-methyl-($\eta^5$-4,5-tetrahydropentalene)]dichlorozirconium, [4-($\eta^5$-cyclopentadienyl)-4-ethyl-($\eta^5$-4,5-tetrahydropentalene)]dichlorozirconium, [4-($\eta^5$-cyclopentadienyl)-4-phenyl-($\eta^5$-4,5-tetrahydropentalene)]dichlorozirconium,

[4-($\eta^5$-cyclopentadienyl)-6-methyl-6-phenyl-($\eta^5$-4,5-tetrahydropentalene)]-dichlorozirconium, [4-($\eta^5$-cyclopentadienyl)-4,6-dimethyl-6-phenyl-($\eta^5$-4,5-tetrahydropentalene)]dichlorozirconium, [4-($\eta^5$-cyclopentadienyl)-4-ethyl-6-methyl-6-phenyl-($\eta^5$-4,5-tetrahydropentalene)]dichlorozirconium, [4-($\eta^5$-cyclopentadienyl)-4-phenyl-6-methyl-6-phenyl-($\eta^5$-4,5-tetrahydropentalene)]dichlorozirconium,

[4-($\eta^5$-cyclopentadienyl)-6,6-diphenyl-($\eta^5$-4,5-tetrahydropentalene)]-dichlorozirconium, [4-($\eta^5$-cyclopentadienyl)-4-methyl-6,6-diphenyl-($\eta^5$-4,5-tetrahydropentalene)]dichlorozirconium, [4-($\eta^5$-cyclopentadienyl)-4,6,6-triphenyl-($\eta^5$-4,5-tetrahydropentalene)]-dichlorozirconium,

[4-($\eta^5$-cyclopentadienyl)-6,6-dimethyl-($\eta^5$-4,5-tetrahydropentalene)]-dichlorozirconium, [4-($\eta^5$-cyclopentadienyl)-4-phenyl-6,6-dimethyl-($\eta^5$-4,5-tetrahydropentalene)]dichlorozirconium,

[4-($\eta^5$-cyclopentadienyl)-6-methyl-($\eta^5$-4,5-tetrahydropentalene)]dichlorozirconium, [4-($\eta^5$-cyclopentadienyl)-6-butyl-($\eta^5$-4,5-tetrahydropentalene)]dichlorozirconium, [4-($\eta^5$-cyclopentadienyl)-6-phenyl-($\eta^5$-4,5-tetrahydropentalene)]dichlorozirconium,

[4-($\eta^5$-cyclopentadienyl)-4,6-dimethyl-($\eta^5$-4,5-tetrahydropentalene)]dichlorozirconium, [4-($\eta^5$-cyclopentadienyl)-4-phenyl-6-methyl-($\eta^5$-4,5-tetrahydropentalene)]-dichlorozirconium,

[4-($\eta^5$-cyclopentadienyl)-4-methyl-6-phenyl-($\eta^5$-4,5-tetrahydropentalene)]-dichlorozirconium, [4-($\eta^5$-cyclopentadienyl)-4-phenyl-6-phenyl-($\eta^5$-4,5-tetrahydropentalene)]-dichlorozirconium,

[4-($\eta^5$-indenyl)($\eta^5$-4,5-tetrahydropentalene)] dichlorotitanium, [4-($\eta^5$-indenyl)($\eta^5$-4,5-tetrahydropentalene)]dichlorozirconium, [4-($\eta^5$-indenyl)($\eta^5$-4,5-tetrahydropentalene)] dichlorohafnium,

[4-($\eta^5$-indenyl)-4-methyl-($\eta^5$-4,5-tetrahydropentalene)] dichlorozirconium, [4-($\eta^5$-indenyl)-4-phenyl-($\eta^5$-4,5-tetrahydropentalene)]dichlorozirconium,

[4-($\eta^5$-indenyl)-6-methyl-6-phenyl-($\eta^5$-4,5-tetrahydropentalene)]dichlorozirconium, [4-($\eta^5$-indenyl)-4,6-dimethyl-6-phenyl-($\eta^5$-4,5-tetrahydropentalene)]dichlorozirconium, [4-($\eta^5$-indenyl)-4-phenyl-6-methyl-6-phenyl-($\eta^5$-4,5-tetrahydropentalene)]-dichlorozirconium,

[4-($\eta^5$-indenyl)-6,6-diphenyl-($\eta^5$-4,5-tetrahydropentalene)]dichlorozirconium, [4-($\eta^5$-indenyl)-4-methyl-6,6-diphenyl-($\eta^5$-4,5-tetrahydropentalene)]-dichlorozirconium, [4-($\eta^5$-indenyl)-4,6,6-triphenyl-($\eta^5$-4,5-tetrahydropentalene)]-dichlorozirconium,

[4-($\eta^5$-indenyl)-6,6-dimethyl-($\eta^5$-4,5-tetrahydropentalene)]dichlorozirconium, [4-($\eta^5$-indenyl)-4-ethyl-6,6-dimethyl-($\eta$-4,5-tetrahydropentalene)]-dichlorozirconium, [4-($\eta^5$-indenyl)-4-phenyl-6,6-dimethyl-($\eta^5$-4,5-tetrahydropentalene)]-dichlorozirconium,

[4-($\eta^5$-indenyl)-6-methyl-($\eta^5$-4,5-tetrahydropentalene)] dichlorozirconium, [4-($\eta^5$-indenyl)-6-ethyl-($\eta^5$-4,5-tetrahydropentalene)]dichlorozirconium, [4-($\eta^5$-indenyl)-6-phenyl-($\eta^5$-4,5-tetrahydropentalene)] dichlorozirconium,

[4-($\eta^5$-indenyl)-4,6-dimethyl-($\eta^5$-4,5-tetrahydropentalene)]dichlorozirconium, [4-($\eta^5$-indenyl)-4-phenyl-6-methyl-($\eta^5$-4,5-tetrahydropentalene)]dichlorozirconium,

[4-($\eta^5$-indenyl)-4-methyl-6-phenyl-($\eta^5$-4,5-tetrahydropentalene)]dichlorozirconium, [4-($\eta^5$-indenyl)-4-phenyl-6-phenyl-($\eta^5$-4,5-tetrahydropentalene)]dichlorozirconium, [4-($\eta^5$-fluorenyl)($\eta^5$-4,5-tetrahydropentalene)] dichlorotitanium, [4-($\eta^5$-fluorenyl)($\eta^5$-4,5-tetrahydropentalene)]dichlorozirconium, [4-($\eta^5$-fluorenyl)($\eta^5$-4,5- tetrahydropentalene)]dichlorohafnium,

[4-($\eta^5$-fluorenyl)-4-methyl-($\eta^5$-4,5-tetrahydropentalene)] dichlorozirconium, [4-($\eta^5$-fluorenyl)-4-phenyl-($\eta^5$-4,5-tetrahydropentalene)]dichlorozirconium,

[4-($\eta^5$-fluorenyl)-6-methyl-6-phenyl-($\eta^5$-4,5-tetrahydropentalene)]dichlorozirconium, [4-($\eta^5$-fluorenyl)-4,6-dimethyl-6-phenyl-($\eta^5$-4,5-tetrahydropentalene)]-dichlorozirconium, [4-($\eta^5$-fluorenyl)-4-phenyl-6-methyl-6-phenyl-($\eta^5$-4,5-tetrahydropentalene)]dichlorozirconium,

[4-($\eta^5$-fluorenyl)-6,6-diphenyl-($\eta^5$-4,5-tetrahydropentalene)]dichlorozirconium, [4-($\eta^5$-fluorenyl)-4-methyl-6,6-diphenyl-($\eta^5$-4,5-tetrahydropentalene)]dichlorozirconium, [4-($\eta^5$-fluorenyl)-4,6,6-triphenyl-($\eta^5$-4,5-tetrahydropentalene)]dichlorozirconium,

[4-($\eta^5$-fluorenyl)-6,6-dimethyl-($\eta^5$-4,5-tetrahydropentalene)]dichlorozirconium, [4-($\eta^5$-fluorenyl)-4-phenyl-6,6-dimethyl-($\eta^5$-4,5-tetrahydropentalene)]-dichlorozirconium,

[4-($\eta^5$-fluorenyl)-6-methyl-($\eta^5$-4,5-tetrahydropentalene)] dichlorozirconium, [4-($\eta^5$-fluorenyl)-6-phenyl-($\eta^5$-4,5-tetrahydropentalene)]dichlorozirconium,

[4-($\eta^5$-fluorenyl)-4,6-dimethyl-($\eta^5$-4,5-tetrahydropentalene)]dichlorozirconium, [4-($\eta^5$-fluorenyl)-4-phenyl-6-methyl-($\eta^5$-4,5-tetrahydropentalene)]dichlorozirconium, [4-($\eta^5$-fluorenyl)-4-methyl-6-phenyl-($\eta^5$-4,5-tetrahydropentalene)]dichlorozirconium, [4-($\eta^5$-fluorenyl)-4-phenyl-6-phenyl-($\eta^5$-4,5-tetrahydropentalene)]dichlorozirconium, [4-($\eta^5$-3,5,6,7-tetrahydroindenyl)($\eta^5$-4,5-tetrahydropentalene)] dichlorotitanium, [4-($\eta^5$-4,5,6,7-tetrahydroindenyl)($\eta^5$-4,5-tetrahydropentalene)]dichlorozirconium, [4-($\eta^5$-4,5,6,7-tetrahydroindenyl)($\eta^5$-4,5-tetrahydropentalene)]dichlorohafnium,

[4-($\eta^5$-4,5,6,7-tetrahydroindenyl)-4-methyl-($\eta^5$-4,5-tetrahydropentalene)]-dichlorozirconium, [4-($\eta^5$-4,5,6,7-tetrahydroindenyl)-4-phenyl-($\eta^5$-4,5-tetrahydropentalene)]-dichlorozirconium,

[4-($\eta^5$-4,5,6,7-tetrahydroindenyl)-6-methyl-6-phenyl-($\eta^5$-4,5-tetrahydropentalene)]dichlorozirconium, [4-($\eta^5$-4,5,6,7-tetrahydroindenyl)-4,6-dimethyl-6-phenyl-($\eta^5$-4,5-tetrahydropentalene)]dichlorozirconium, [4-($\eta^5$-4,5,6,7-tetrahydroindenyl)-4-phenyl-6-methyl-6-phenyl-($\eta^5$-4,5-tetrahydropentalene)] dichlorozirconium,

[4-($\eta^5$-4,5,6,7-tetrahydroindenyl)-6,6-diphenyl-($\eta^5$-4,5-tetrahydropentalene)]dichlorozirconium, [4-($\eta^5$-4,5,6,7-tetrahydroindenyl)-4-methyl-6,6-diphenyl-($\eta^5$-4,5-tetrahydropentalene)]dichlorozirconium, [4-($\eta^5$-4,5,6,7-tetrahydroindenyl)-4,6,6-triphenyl-($\eta^5$-4,5-tetrahydropentalene)]dichlorozirconium,

[4-($\eta^5$-4,5,6,7-tetrahydroindenyl)-6,6-dimethyl-($\eta^5$-4,5-tetrahydropentalene)]dichlorozirconium, [4-($\eta^5$-4,5,6,7-tetrahydroindenyl)-4-ethyl-6,6-dimethyl-($\eta^5$-4,5-tetrahydropentalene)]dichlorozirconium, [4-($\eta^5$-4,5,6,7-tetrahydroindenyl)-4-phenyl-6,6-dimethyl-($\eta^5$-4,5-tetrahydropentalene)]dichlorozirconium,

[4-($\eta^5$-4,5,6,7-tetrahydroindenyl)-6-methyl-($\eta^5$-4,5-tetrahydropentalene)]-dichlorozirconium, [4-($\eta^5$-4,5,6,7-tetrahydroindenyl)-6-phenyl-($\eta^5$-4,5-tetrahydropentalene)]-dichlorozirconium,

[4-($\eta^5$-4,5,6,7-tetrahydroindenyl)-4,6-dimethyl-($\eta^5$-4,5-tetrahydropentalene)]dichlorozirconium, [4-($\eta^5$-4,5,6,7-tetrahydroindenyl)-4-phenyl-6-methyl-($\eta^5$-4,5-tetrahydropentalene)]dichlorozirconium,

[4($\eta^5$-4,5,6,7-tetrahydroindenyl)-4-methyl-6-phenyl-($\eta^5$-4,5-tetrahydropentalene)]dichlorozirconium, [4-($\eta^5$-4,5,6,7-tetrahydroindenyl)-4-phenyl-6-phenyl-($\eta^5$-4,5-tetrahydropentalene)]dichlorozirconium,

[4-($\eta^5$-3'-methylcyclopentadienyl)-($\eta^5$-4,5-tetrahydropentalene)]dichlorozirconium, [4-($\eta^5$-3'-isopropylcyclopentadienyl)-($\eta^5$-4,5-tetrahydropentalene)]dichlorozirconium, [4-($\eta^5$-3'-benzylcyclopentadienyl)-($\eta^5$-4,5-tetrahydropentalene)]dichlorozirconium,

[4-($\eta^5$-3'-methylcyclopentadienyl)-4-methyl-($\eta^5$-4,5-tetrahydropentalene)]-dichlorozirconium, [4-($\eta^5$-3'-isopropylcyclopentadienyl)-4-methyl-($\eta^5$-4,5-tetrahydropentalene)]dichlorozirconium, [4-($\eta^5$-3'-benzylcyclopentadienyl)-4-methyl-($\eta^5$-4,5-tetrahydropentalene)]-dichlorozirconium,

[4-($\eta^5$-3'-methylcyclopentadienyl)-4-phenyl-($\eta^5$-4,5-tetrahydropentalene)]-dichlorozirconium, [4-($\eta^5$-3'-isopropylcyclopentadienyl)-4-phenyl-($\eta^5$-4,5-tetrahydropentalene)]dichlorozirconium, [4-($\eta^5$-3'-benzylcyclopentadienyl)-4-phenyl-($\eta^5$-4,5-tetrahydropentalene)]-dichlorozirconium,

[4-($\eta^5$-3'-methylcyclopentadienyl)-4,6-dimethyl-($\eta^5$-4,5-tetrahydropentalene)]dichlorozirconium, [4-($\eta^5$-3'-isopropylcyclopentadienyl)-4,6-dimethyl-($\eta^5$-4,5-tetrahydropentalene)]dichlorozirconium, [4-($\eta^5$-3'-benzylcyclopentadienyl)-4,6-dimethyl-($\eta^5$-4,5-tetrahydropentalene)]dichlorozirconium,

[4-($\eta^5$-3'-methylcyclopentadienyl)-4-methyl-6-phenyl-($\eta^5$-4,5-tetrahydropentalene)]dichlorozirconium, [4-($\eta^5$-3'-isopropylcyclopentadienyl)-4-methyl-6-phenyl-($\eta^5$-4,5-tetrahydropentalene)]dichlorozirconium, [4-($\eta^5$-3'-benzylcyclopentadienyl)-4-methyl-6-phenyl-($\eta^5$-4,5-tetrahydropentalene)]dichlorozirconium,

[4-($\eta^5$-3'-methylcyclopentadienyl)-4,6-dimethyl-6-phenyl-($\eta^5$-4,5-tetrahydropentalene)] dichlorozirconium, [4-($\eta^5$-3'-isopropylcyclopentadienyl)-4,6-dimethyl-6-phenyl-($\eta^5$-4,5-tetrahydropentalene)]dichlorozirconium, [4-($\eta^5$-3'-benzylcyclopentadienyl)-4,6-dimethyl-6-phenyl-($\eta^5$-4,5-tetrahydropentalene)] dichlorozirconium,

[4-($\eta^5$-3'-methylcyclopentadienyl)-2-methyl-($\eta^5$-4,5-tetrahydropentalene)]-dichlorozirconium, [4-($\eta^5$-3'-isopropylcyclopentadienyl)-2-isopropyl-($\eta^5$-4,5-tetrahydropentalene)]dichlorozirconium, [4-($\eta^5$-3'-benzylcyclopentadienyl)-2-benzyl-($\eta^5$-4,5-tetrahydropentalene)]-dichlorozirconium, [4-($\eta^5$-3'-isopropylcyclopentadienyl)-2-benzyl-($\eta^5$-4,5-tetrahydropentalene)]dichlorozirconium, [4-($\eta^5$-3'-benzylcyclopentadienyl)-2-isopropyl-($\eta^5$-4,5-tetrahydropentalene)]dichlorozirconium,

[4-($\eta^5$-3'-methylcyclopentadienyl)-2,4-dimethyl-($\eta^5$-4,5-tetrahydropentalene)]dichlorozirconium, [4-($\eta^5$-3'-isopropylcyclopentadienyl)-2-isopropyl-4-methyl-($\eta^5$-4,5-tetrahydropentalene)]dichlorozirconium, [4-($\eta^5$-3'-benzylcyclopentadienyl)-2-benzyl-4-methyl-($\eta^5$-4,5-tetrahydropentalene)]dichlorozirconium,

[4-($\eta^5$-3'-isopropylcyclopentadienyl)-2-benzyl-4-methyl-($\eta^5$-4,5-tetrahydropentalene)]dichlorozirconium, [4-($\eta^5$-3'-benzylcyclopentadienyl)-2-isopropyl-4-methyl-($\eta^5$-4,5-tetrahydropentalene)]dichlorozirconium.

* * * * *

UNITED STATES PATENT AND TRADEMARK OFFICE

CERTIFICATE OF CORRECTION

PATENT : 6,063,949

DATED : May 16, 2000

INVENTOR(S) : Michael Aulbach, Frank Kuber, Michael Riedel and Freddy Helmer-Metzmann It is certified that error appears in the above-identified patent and that said Letters Patent is hereby corrected as shown below:

In claim 2, column 26, line 63, insert the word - - and - - after "dichlorozirconium".

Signed and Sealed this

Twentieth Day of March, 2001

Attest:

NICHOLAS P. GODICI

*Attesting Officer* *Acting Director of the United States Patent and Trademark Office*